US009833439B2

(12) United States Patent
Charbonnier et al.

(10) Patent No.: US 9,833,439 B2
(45) Date of Patent: Dec. 5, 2017

(54) ERK INHIBITORS FOR USE IN TREATING SPINAL MUSCULAR ATROPHY

(75) Inventors: Frédéric Charbonnier, Paris (FR); Olivier Biondi, Boissise la Bertrand (FR)

(73) Assignees: UNIVERSITE PARIS DESCARTES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/119,906

(22) PCT Filed: May 24, 2012

(86) PCT No.: PCT/EP2012/059685
§ 371 (c)(1),
(2), (4) Date: Jan. 13, 2014

(87) PCT Pub. No.: WO2012/160130
PCT Pub. Date: Nov. 29, 2012

(65) Prior Publication Data
US 2014/0113956 A1 Apr. 24, 2014

Related U.S. Application Data

(60) Provisional application No. 61/489,721, filed on May 25, 2011.

(51) Int. Cl.
*A61K 38/00* (2006.01)
*A61K 48/00* (2006.01)
(Continued)

(52) U.S. Cl.
CPC ........ *A61K 31/4184* (2013.01); *A61K 31/136* (2013.01); *A61K 31/16* (2013.01); *A61K 31/166* (2013.01); *A61K 31/352* (2013.01); *A61K 31/4412* (2013.01); *A61K 31/7088* (2013.01); *A61K 31/713* (2013.01)

(58) Field of Classification Search
USPC .................................. 514/2, 44 A; 536/24.5
See application file for complete search history.

(56) References Cited

U.S. PATENT DOCUMENTS 5,525,625 A  6/1996 Bridges et al.
6,506,559 B1  1/2003 Fire et al.
(Continued)

FOREIGN PATENT DOCUMENTS

EP  2275102 A1  1/2011
WO  WO 98/43960  10/1998
(Continued)

OTHER PUBLICATIONS

Adjei et al. (Journal of Clinical Oncology, 2008 vol. 26:2139-2146).*
(Continued)

*Primary Examiner* — Terra C Gibbs
(74) *Attorney, Agent, or Firm* — Seyfarth Shaw LLP

(57) ABSTRACT

The present invention relates to a method for treating spinal muscular atrophy and other related neuromuscular disorders in a subject in need thereof, said method comprising administering a therapeutically effective amount of an ERK inhibitor, such as Selumetinib to said subject.

12 Claims, 16 Drawing Sheets

Figure 1:
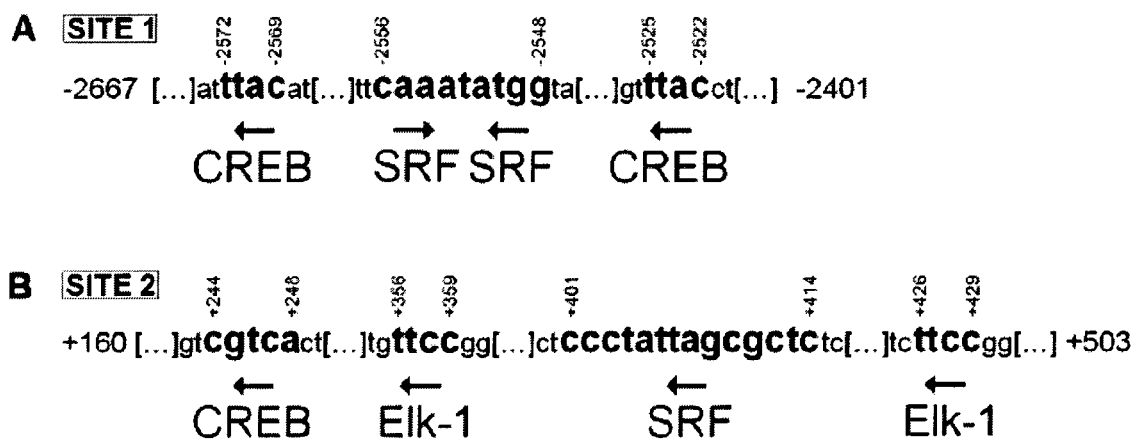
Figure 1:
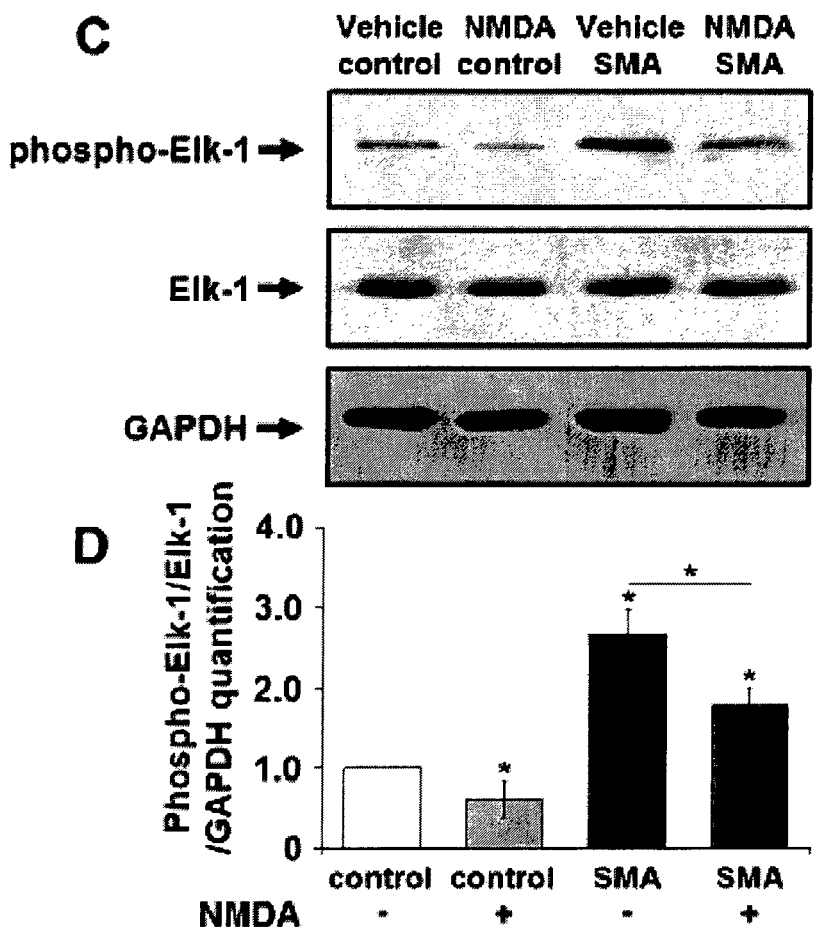
Figure 1:
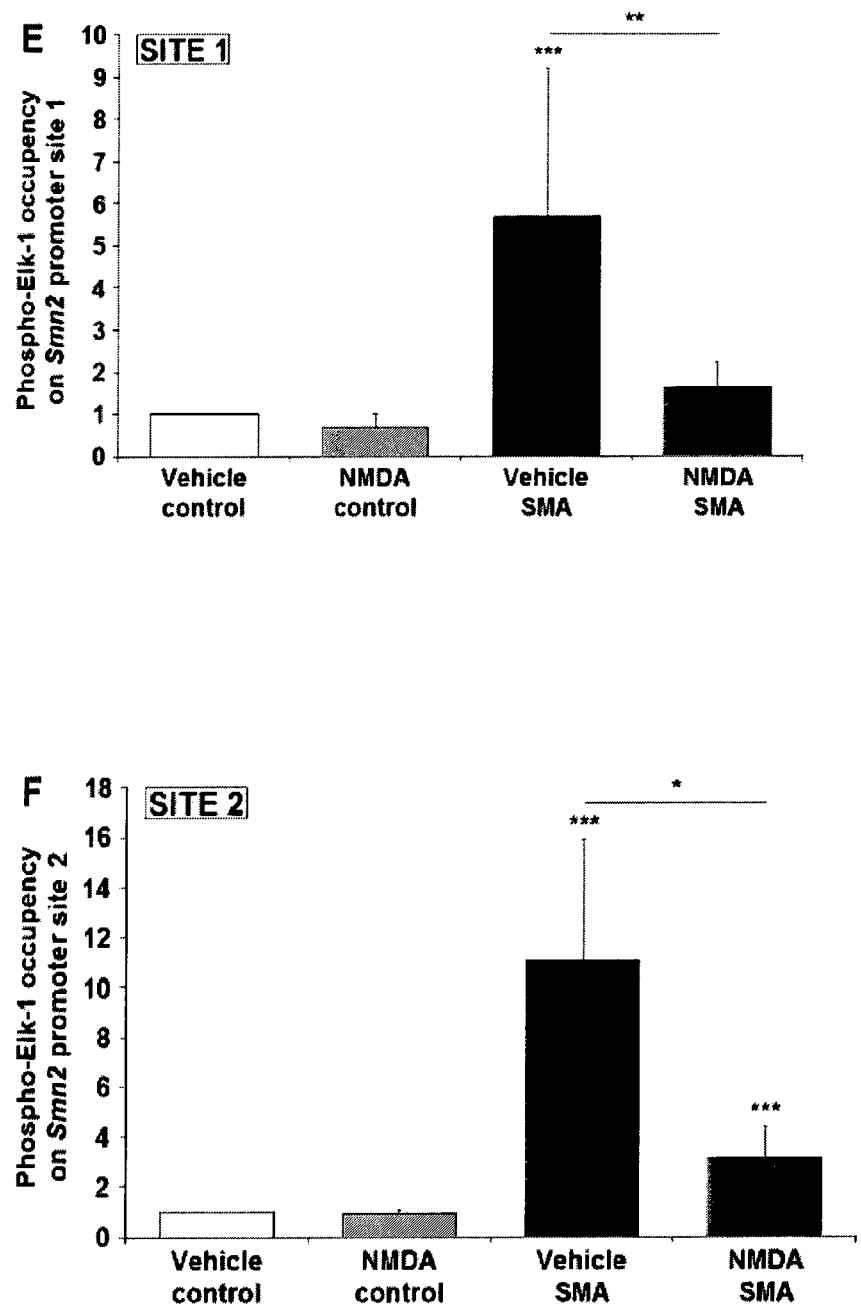
Figure 1:
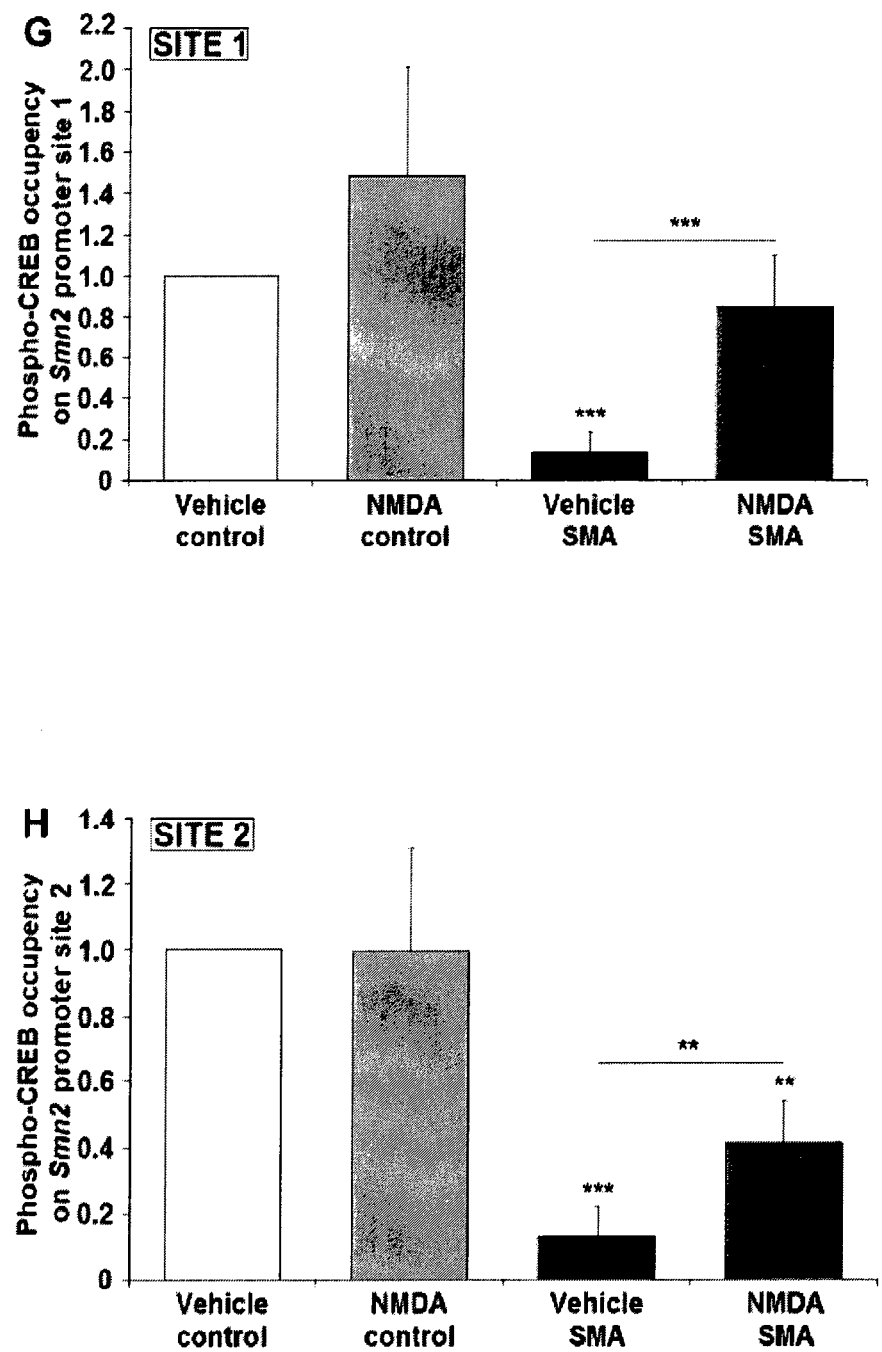
Figure 1:
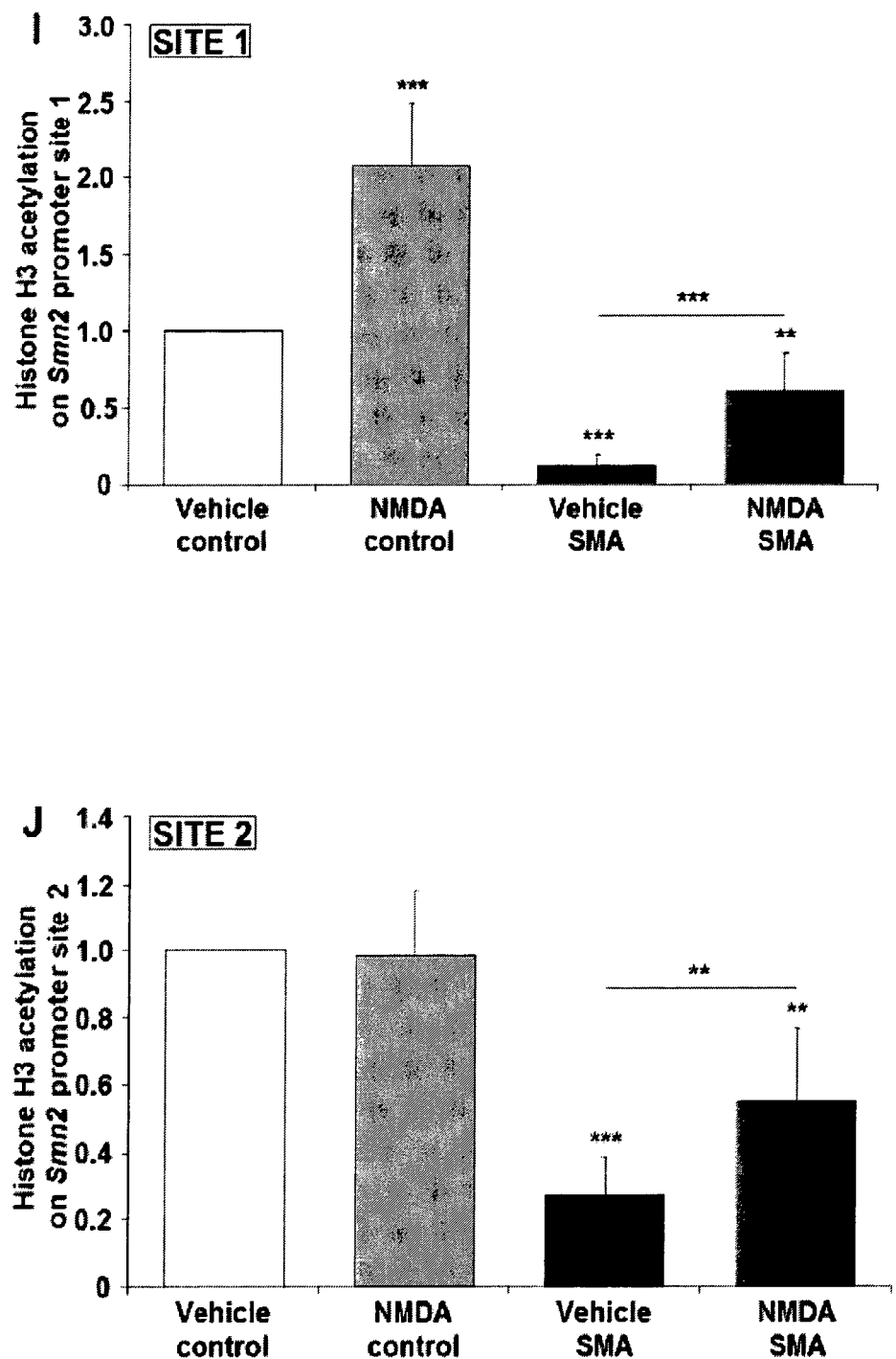
Figure 1:
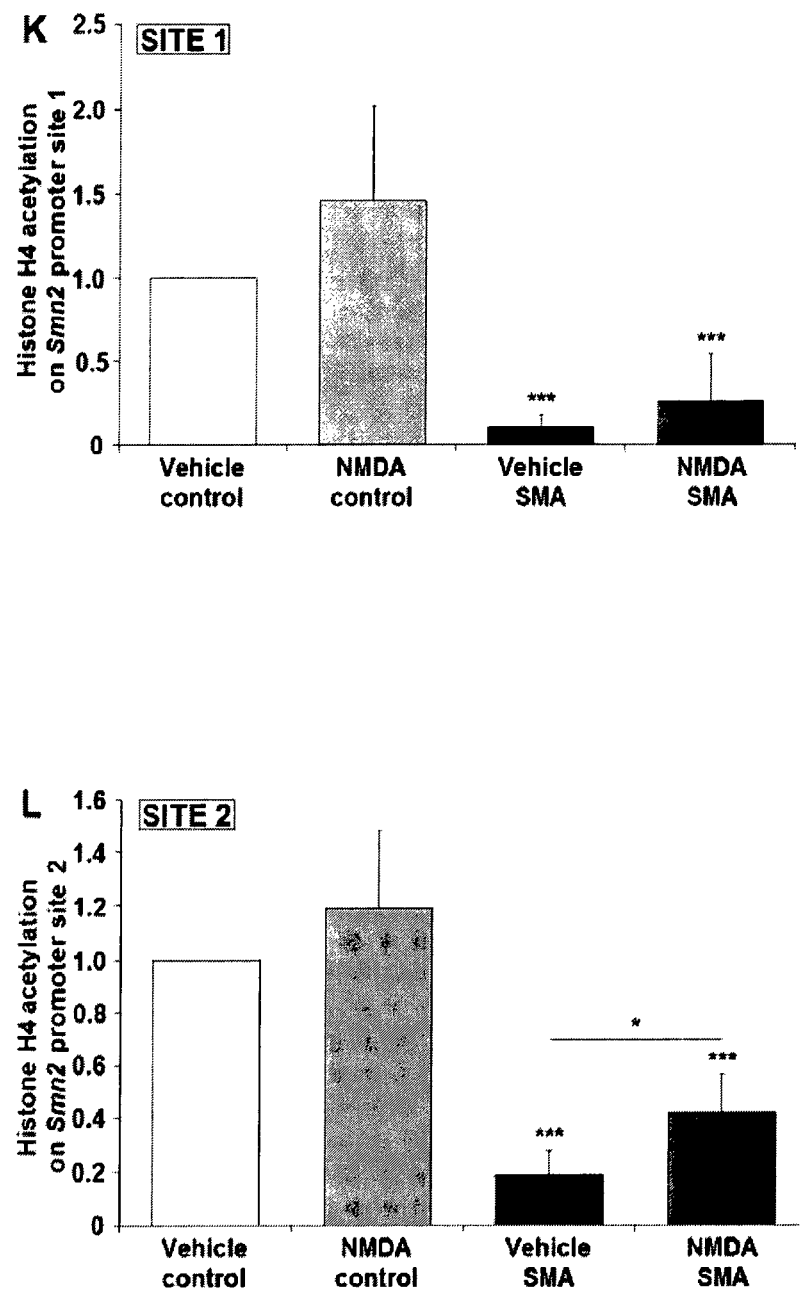

(51) Int. Cl.
| | |
|---|---|
| A61K 31/4184 | (2006.01) |
| A61K 31/136 | (2006.01) |
| A61K 31/16 | (2006.01) |
| A61K 31/166 | (2006.01) |
| A61K 31/352 | (2006.01) |
| A61K 31/4412 | (2006.01) |
| A61K 31/713 | (2006.01) |
| A61K 31/7088 | (2006.01) |

(56) References Cited

U.S. PATENT DOCUMENTS

| | | |
|---|---|---|
| 6,573,099 B2 | 6/2003 | Graham |
| 2003/0060469 A1 | 3/2003 | Ludwig et al. |
| 2004/0048861 A1 | 3/2004 | Bemis et al. |
| 2004/0082631 A1 | 4/2004 | Hale et al. |
| 2006/0140872 A1* | 6/2006 | Furue ............ A61K 31/275 424/45 |
| 2007/0292408 A1 | 12/2007 | Singh et al. |

FOREIGN PATENT DOCUMENTS

| | | |
|---|---|---|
| WO | WO 99/01426 | 1/1999 |
| WO | WO 99/32619 | 7/1999 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/68201 | 11/2000 |
| WO | WO 01/36646 | 5/2001 |
| WO | WO 01/68619 | 9/2001 |
| WO | WO 01/68836 | 9/2001 |
| WO | WO 02/06213 | 1/2002 |
| WO | WO 02/055693 | 7/2002 |
| WO | WO 02/094842 A2 | 11/2002 |
| WO | WO 2002/094842 A2 | 11/2002 |
| WO | WO 03/077855 | 9/2003 |
| WO | WO 03/077914 | 9/2003 |
| WO | WO 2005/023251 | 3/2005 |
| WO | WO 2009/036020 A1 | 3/2009 |
| WO | WO 2010/148249 A1 | 12/2010 |
| WO | WO 2010/151638 | 12/2010 |
| WO | WO 2012/160130 A1 | 11/2012 |

OTHER PUBLICATIONS

Passini, et al., "Antisense oligonucleotides delivered to the mouse CNS ameliorate symptoms of severe spinal muscular atrophy", Science Translational Medicine, vol. 3, No. 72, Mar. 2, 2011, p. 72RA18, XP9161512.
Millino, et al, "Different atrophy-hypertrophy transcription pathways in muscles affected by severe and mild spinal muscular atrophy", BMC Medicine, Biomed Central Ltd., vol. 7, No. 1, Apr. 7, 2009, pp. 14-22, XP02105136.
International Search Report for Int'l Appl. No. PCT/EP2012/059685, dated on Aug. 3, 2012.
International Report on Patentability for Int'l Appl. No. PCT/EP2012/059685, issued on Nov. 26, 2013.
Avila, A. M. et al., "Trichostatin a increases SMN expression and survival in a mouse model of spinal muscular atrophy," *J. Clin. Invest.*, 117:659-671, 2007.
Adjei et al., "Phase I Pharmacokinetic and Pharmacodynamic Study of the Oral, Small-Molecule Mitogen —Activated Protein Kinase Kinase 1/2 Inhibitor AZD6244 (ARRY-142886) in Patients With Advanced Cancers," *J Clin Oncol*, 26:2139-2146, 2008.
Ahn N. et al., "U0126: an Inhibitor of MKK/ERK Signal Transduction in Mammalian Cells," *Promega Notes.*, 71:4, 1999.
Bigot, A. et al., "Large CTG repeats trigger p16-dependent premature senescence in myotonic dystrophy type 1 muscle precursor cells," *Am. J. Pathol.*,174:1435-1442, 2009.
Brummelkamp, T R. et al., "A System for Stable Expression of Short Interfering RNAs," *Science*, 296:550-553, 2002.
Biondi, O. et al., "In vivo NMDA receptor activation accelerates motor unit maturation, protects spinal motor neurons, and enhances SMN2 gene expression in severe spinal muscular atrophy mice," *J. Neurosci.*, 30:11288-11299, 2010.
Board, R. E. et al., "Detection of BRAF mutations in the tumour and serum of patients enrolled in the AZD6244 (ARRY-142886) advanced melanoma phase II study," *Br. J. Cancer*, 101:1724-1730, 2009.
Butchbach, M. E. et al., "Effect of diet on the survival and phenotype of a mouse model for spinal muscular atrophy," *Biochem. Biophys. Res. Commun.*, 391:835-840, 2010.
Chen, F. et al., "Characterization of ATP-independent ERK inhibitors identified through in silico analysis of the active ERK2 structure," *Bioorg. Med. Chem.*, 16:6281-6288, 2006.
Crawford, T. O. & Pardo, C. A., "The neurobiology of childhood spinal muscular atrophy," *Neurobiol. Dis.*3:97-110, 1996.
Chang, J. G. et al., "Treatment of spinal muscular atrophy by sodium butyrate," *Proc. Natl. Acad. Sci. U.S.A.*, 98:9808-9813, 2001.
DeSilva, D. R., et al. Inhibition of Mitogen-Activated Protein Kinase Kinase Blocks T Cell Proliferation But Does Not Induce or Prevent Anergy, *J. Immunol.*, 160:4175-4181, 1998.
Demir, O. et al., "ETS-domain transcription factor Elk-1 mediates neuronal survival: SMN as a potential target," *Biochim. Biophys. Acta*, 1812:652-662, 2011.
Duncia, J. V., et al., "MEK Inhibitors: The Chemistry and Biological Activity of U0126, It's Analogs, and Cyclization Produtcts," *Bioorg. Med. Chem. Left.*, 8:2839, 1998.
Dudek, H. et al., "Regulation of neuronal survival by the serine-threonine protein kinase AKT, " *Science*, 275:661-665, 1997.
Elbashir, S. M. et al, "Duplexes of 21-nucleotide RNAs mediate RNA interference in cultured mammalian cells," *Letters to Nature*, 411:494-498, 2001.
Favata, M. F., et al., "Identification of a Novel Inhibitor of Mitogen-activated Protein Kinase Kinase," *J. Biol. Chem.*, 273:18623, 1998.
Hancock, C N. et al., Identification of Novel Extracellular Signal-Regulated Kinase Docking Domain Inhibitors, *J. Med. Chem.*, 48:4586-4595, 2005.
Hannon, G J., "RNA Interference," *Nature*, 418:244-51, 2002.
Kohno M. & Pouyssegur, J., "Pharmacological inhibitors of the ERK signaling pathway: application as anticancer drugs," *Prog. Cell. Cyc. Res.*, 5: 219-224, 2003.
Knockhaert M. et al., "p42/p44 MAPKs are intracellular targets of the CDK inhibitor purvalanol," *Oncogene*, 21:6413-6424, 2002.
Kobayashi, T., "Human muscle cultured in monolayer and cocultured with fetal rat spinal cord: importance of dorsal root ganglia for achieving successful functional innervation," *J. Neurosci*, 7: 3131-3141,1987.
Kolb, E. A, et al., "Initial testing (stage 1) of AZD6244 (ARRY-142886) by the Pediatric Preclinical Testing Program, " *Pediatr. Blood Cancer*, 55:668-677, 2010.
Kolb, E.A., "A homogeneous time resolved fluorescence method for drug discovery" in: High Throughput screening: the discovery of bioactive substances. J. Devlin. NY, Marcel Dekker 345-360, 1997.
Lefebvre, S. et al., "Identification and characterization of a spinal muscular atrophy-determining gene," *Cell*, 80:155-165, 1995.
Lorson, C. L. et al., "An exonic enhancer is required for inclusion of an essential exon in the SMA-determining gene SMN," *Hum. Mol. Genet.*, 9:259-265, 2000.
Lorson, C. L., et al., "M. Spinal muscular atrophy: mechanisms and therapeutic strategies," *Hum. Mol. Genet.*, 19:R111-R118, 2010.
Majumder, S. et al., "Identification of a novel cyclic AMP-response element (CRE-II) and the role of CREB-1 in the cAMP-induced expression of the survival motor neuron (SMN) gene," *J. Biol. Chem.*, 279:14803-14811, 2004.
Mercuri, E. et al., " Randomized, double-blind, placebo-controlled trial of phenylbutyrate in spinal muscular atrophy," *Neurology*, 68: 51-55, 2007.
McManus, M T.et al., "Small Interfering RNA-Mediated Gene Silencing in T Lymphocytes," *J Immunol.*, 169:5754-5760, 2002.

(56) References Cited

OTHER PUBLICATIONS

Millino, Caterina et al., "Different atrophy-hypertrophy transcription pathways in muscles affected by severe and mild spinal muscular atrophy," *BMC Medicine*, 7:14-22, Apr. 7, 2009.
Monani, U. R. et al., "The human centromeric survival motor neuron gene (SMN2) rescues embryonic lethality in SMNn(-/-) mice and results in a mouse with spinal muscular atrophy," *Hum. Mol. Genet.*, 9: 333-339, 2000.
Ohori, M. et al., Identification of a selective ERK inhibitor and structural determination of the inhibitor-ERK2 complex, *Biochem. Biophys. Res. Comm.*, 336:357-363, 2005.
M. A. Passini et al., "Antisense oligonucleotides delivered to the mouse CNS ameliorate symptoms of several spinal muscular atrophy," Science Translational Medicine, 3:72:72RA18, Abstract, Mar. 2, 2011.
Runden E et al., Regional Selective Neuronal Degeneration after Protein Phosphatase Inhibition in Hippocampla Slice Cultures: Evidence for a MAP Kinase-Dependent Mechanism, *J Neurosci*, 18: 7296-305, 1998.
Schwarze et al., "In Vivo Protein Transduction: Delivery of a Biologically Active Protein into the Mouse," *Science.* 285:1569-72, 1999.
Soler, R. M. et al., "Receptors of the glial cell line-derived neurotrophic factor family of neurotrophic factors signal cell survival through the phosphatidylinositol 3-kinase pathway in spinal cord motoneurons," *J. Neurosci.* 19:9160-9169, 1999.
Swoboda, K. J. et al., "Phase II Open Label Study of Valproic Acid in Spinal Muscular Atrophy," PLoS One, 4:e5268. (2009).
Swoboda, K. J. et al., "SMA CARNI-VAL Trial Part I: Double-Blind, Randomized, Placebo-Controlled Trial of L-Carnitine and Valproic Acid in Spinal Muscular Atrophy," Project Cure Spinal Muscular Atrophy Investigators Network, PloS One, 5:e12140, 2010.

Tsai, L. K., "Multiple therapeutic effects of valproic acid in spinal muscular atrophy model mice," *J. Mol. Med.*, 86:1243-1254, 2008.
Thurmond, J. et al., Synthesis and biological evaluation of novel 2,4-diaminoquinazoline derivatives as SMN2 promoter activators for the potential treatment of spinal muscular atrophy, *J. Med. Chem.* 51:449-469, 2008.
Towbin, H. et al., "Glycosphingolipid-blotting: an immunological detection procedure after separation by thin layer chromatography", *J. lmmunol. Methods*, 72: 471-479, 1984.
Tuschl, T. et al., "Targeted mRNA degradation by double-stranded RNA in vitro," *Genes Dev.* 13:3191-3197, 1999.
Williams et al., "RO 09-2210 Exhibits Potent Anti-proliferative Effects on Activated T Cells by Selectively Blocking MKK Activity," *Biochemistry*, 37:9579-85, 1998.
Whitmarsh, a. J., et al., "Integration of MAP kinase signal transduction pathways at the serum response element", *Science*, 269: 403-407,1995.
Xia, Z., et al., "Opposing effects of ERK and JNK-p38 MAP kinases on apoptosis," *Science*, 270:1326-1331, 1995.
Yang, S. H., et al., "The mechanism of phosphorylation-inducible activation of the ETS-domain transcription factor Elk-1", *Embo J.*, 18:5666-5674, 1999.
Zhang N. et al., "Synthesis and Structure-Activity Relationships of 3-Cyano-4-(phneoxyanilino) quinolones as MEK (MAPKK) Inhibitors," *Bioorg Med. Chem. Lett.*, 10: 2825-2828, 2000.
Zhang, H. M., "Mitogen-induced recruitment of ERK and MSK to SRE promoter complexes by ternary complex factor Elk-1," *Nucleic Acids Res.*, 36:2594-2607, 2008.
Zhao a. et al., "Resorcylic Acid Lactones: Naturally Occurring Potent and Selective Inhibitors of MEK," *J. Antibiot.*, 52:1086-1094, 1999.

* cited by examiner

SEQUENCE LISTING

<160> NUMBER OF SEQ ID NOS: 7

<210> SEQ ID NO 1
<211> LENGTH: 393
<212> TYPE: PRT
<213> ORGANISM: Homo sapiens

<400> SEQUENCE: 1

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365
```

```
Val Asp Phe Ala Gly Trp Leu Cys Ser Thr Ile Gly Leu Asn Gln Pro
370                 375                 380

Ser Thr Pro Thr His Ala Ala Gly Val
385                 390
```

<210> SEQ ID NO 2
<211> LENGTH: 400
<212> TYPE: PRT
<213> ORGANISM: Homo sapiens

<400> SEQUENCE: 2

```
Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
                20                  25                  30

Asn Leu Val Asp Leu Gln Lys Lys Leu Glu Glu Leu Glu Leu Asp Glu
            35                  40                  45

Gln Gln Lys Lys Arg Leu Glu Ala Phe Leu Thr Gln Lys Ala Lys Val
50                  55                  60

Gly Glu Leu Lys Asp Asp Phe Glu Arg Ile Ser Glu Leu Gly Ala
65                  70                  75                  80

Gly Asn Gly Gly Val Thr Lys Val Gln His Arg Pro Ser Gly Leu
                85                  90                  95

Ile Met Ala Arg Lys Leu Ile His Leu Glu Ile Lys Pro Ala Ile Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350
```

```
Asn Pro Ala Glu Arg Ala Asp Leu Lys Met Leu Thr Asn His Thr Phe
        355                 360                 365

Ile Lys Arg Ser Glu Val Glu Val Asp Phe Ala Gly Trp Leu Cys
370                 375                 380

Lys Thr Leu Arg Leu Asn Gln Pro Gly Thr Pro Thr Arg Thr Ala Val
385                 390                 395                 400

<210> SEQ ID NO 3
<211> LENGTH: 379
<212> TYPE: PRT
<213> ORGANISM: Homo sapiens

<400> SEQUENCE: 3

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
```

```
              325                 330                 335
Thr Asp Glu Pro Val Ala Glu Pro Phe Thr Phe Ala Met Glu Leu
            340                 345                 350
Asp Asp Leu Pro Lys Glu Arg Leu Lys Glu Leu Ile Phe Gln Glu Thr
            355                 360                 365
Ala Arg Phe Gln Pro Gly Val Leu Glu Ala Pro
    370                 375
```

<210> SEQ ID NO 4
<211> LENGTH: 360
<212> TYPE: PRT
<213> ORGANISM: Homo sapiens

<400> SEQUENCE: 4

```
Met Ala Ala Ala Ala Ala Gly Ala Gly Pro Glu Met Val Arg Gly
1               5                  10                  15
Gln Val Phe Asp Val Gly Pro Arg Tyr Thr Asn Leu Ser Tyr Ile Gly
                20                  25                  30
Glu Gly Ala Tyr Gly Met Val Cys Ser Ala Tyr Asp Asn Val Asn Lys
            35                  40                  45
Val Arg Val Ala Ile Lys Lys Ile Ser Pro Phe Glu His Gln Thr Tyr
    50                  55                  60
Cys Gln Arg Thr Leu Arg Glu Ile Lys Ile Leu Leu Arg Phe Arg His
65                  70                  75                  80
Glu Asn Ile Ile Gly Ile Asn Asp Ile Ile Arg Ala Pro Thr Ile Glu
                85                  90                  95
Gln Met Lys Asp Val Tyr Ile Val Gln Asp Leu Met Glu Thr Asp Leu
            100                 105                 110
Tyr Lys Leu Leu Lys Thr Gln His Leu Ser Asn Asp His Ile Cys Tyr
        115                 120                 125
Phe Leu Tyr Gln Ile Leu Arg Gly Leu Lys Tyr Ile His Ser Ala Asn
    130                 135                 140
Val Leu His Arg Asp Leu Lys Pro Ser Asn Leu Leu Leu Asn Thr Thr
145                 150                 155                 160
Cys Asp Leu Lys Ile Cys Asp Phe Gly Leu Ala Arg Val Ala Asp Pro
                165                 170                 175
Asp His Asp His Thr Gly Phe Leu Thr Glu Tyr Val Ala Thr Arg Trp
            180                 185                 190
Tyr Arg Ala Pro Glu Ile Met Leu Asn Ser Lys Gly Tyr Thr Lys Ser
        195                 200                 205
Ile Asp Ile Trp Ser Val Gly Cys Ile Leu Ala Glu Met Leu Ser Asn
    210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
                245                 250                 255
Asn Leu Lys Ala Arg Asn Tyr Leu Leu Ser Leu Pro His Lys Asn Lys
            260                 265                 270
Val Pro Trp Asn Arg Leu Phe Pro Asn Ala Asp Ser Lys Ala Leu Asp
        275                 280                 285
Leu Leu Asp Lys Met Leu Thr Phe Asn Pro His Lys Arg Ile Glu Val
    290                 295                 300
Glu Gln Ala Leu Ala His Pro Tyr Leu Glu Gln Tyr Tyr Asp Pro Ser
305                 310                 315                 320
```

-continued

```
Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Pro Lys Lys Lys Pro Thr Pro Ile Gln Leu Asn Pro
1               5                   10

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttcaaatatg gta                                                          13

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctccctatta gcgctctc                                                     18
```

ERK INHIBITORS FOR USE IN TREATING SPINAL MUSCULAR ATROPHY

This application is a National Stage of PCT/EP2012/059685, filed May 24, 2012 which claims priority to U.S. Provisional Application No. 61/489,721, filed May 25, 2011, the disclosures of which are incorporated herein by reference in their entirety.

The instant application contains a Sequence Listing which has been submitted electronically in ASCII format and is hereby incorporated by reference in its entirety. Said ASCII copy, created on Aug. 11, 2014, is named 999500-PD01US1 SL.txt and is 14,372 bytes in size.

FIELD OF THE INVENTION

The present invention relates to a method for treating spinal muscular atrophy and other related neuromuscular disorders in a subject in need thereof, said method comprising administering a therapeutically effective amount of an ERK inhibitor, such as Selumetinib, to said subject in need thereof.

BACKGROUND OF THE INVENTION

Spinal Muscular Atrophy (SMA) is a recessive neurodegenerative disease characterized by the selective loss of spinal motor neurons'. SMA is caused by mutation of the Survival-of-Motor-Neuron 1 (SMN1) gene[2] and deficiency of the survival motor neuron (SMN) protein expression. All patients retain one or more copies of the SMN2 gene, which modulates the disease severity by producing a small amount of full-length SMN transcripts and consequently of stable SMN protein[3]. Since SMA is caused by insufficient amounts of SMN protein, a major aim of SMA therapeutics strategy is to increase SMN protein levels by activating SMN2 gene expression. However, to date there is no available therapy for SMA, which represents the leading genetic cause of death in childhood.

The mode of action of therapeutic molecules for the treatment of SMA may include the increase of SMN expression particularly in motor neurons through activating the SMN2 promoter, increasing exon-7 inclusion in SMN transcripts, or extending the half-life of SMN mRNA or protein.

It may also include the promotion of motor neuron survival through the activation of anti-apoptotic pathways. Over the years, a number of groups have identified SMN2 gene-inducing compounds using cultured fibroblasts derived from SMA patients, and which benefits were often further tested in vivo in SMA mouse models[5]. Among those, SMN inducer compounds were identified based on their supposed ability to increase general gene expression, such as histone deacetylase inhibitors[6, 7, 8], or by high throughput screenings, such as quinazoline derivatives[9, 10]. Unfortunately, to date, many of these compounds were disappointing in clinical trials with no substantial clinical benefit demonstrated[11, 12, 13]. Ultimately, none of these compounds provide efficient anti-apoptotic potential for motor neurons.

One promising, as yet unexplored, therapeutic development for SMA could involve the pharmacological correction of molecular mechanisms, specifically altered in SMA neuromuscular system, potentially capable of modulating either SMN expression, or motor-neuron survival or both.

However, there is still a need to understand the molecular pathways involved in the modulation of SMN expression or motor-neuron survival and identify efficient strategies for treating SMA.

Constitutively down-regulated in mouse SMA spinal cord, the AKT/CREB pathway is able to remarkably alleviate SMA symptoms in mice as long as it is reactivated[14]. In very severe SMA-like mice[15], the reactivation of AKT/CREB pathway by NMDA resulted in an increased in the total amount of SMN transcripts in the SMA spinal cord without modifying its splicing pattern suggesting a SMN2 gene regulation at the transcriptional level[14]. Furthermore, considered as a common and powerful antiapoptotic pathway[16] notably for spinal motor neurons[17], the AKT/CREB pathway activation likely represents an important clue for motor neuron resistance to cell death in SMA spinal cord. Thus, identifying therapeutic agents that could lead to the reactivation of the AKT/CREB pathway in SMA spinal cord has been suggested as a possible approach for treating SMA.

International Patent Publication No. WO2010/148249 (Isis Pharmaceuticals, Genzyme Corp, Cold Spring Harbor Laboratory) describes methods and compositions for modulating splicing of SMN2 mRNA in a subject, for the treatment of spinal muscular atrophy.

Interestingly, the activation profile of another major intracellular signaling pathway in neurons[18], namely the ERK1/2 signaling pathway, was in opposite contrast to that of AKT in SMA spinal cord. Constitutively over-activated in the spinal cord of two different severe mouse models of SMA, characterized by a weak SMN expression, ERK1/2 was inhibited when AKT is reactivated and this change in ERK/AKT activation balance correlated with an increase in SMN expression[14]. However, these data failed to show any direct link between a modulation of ERK 1/2 signaling pathway and SMN2 gene regulation.

ERK inhibitors, such as Selumetinib have been described in the Art for their use in treating cancer disorders (see for example, Adjei et al. J Clin Oncol 2008 26(13):2139-2146; Board et al. Br J Cancer 2009 101(10):1724-30; Kolb et al. Pediatr Blood Cancer 2010 55(4):668-677). To Applicant's knowledge, these molecules have never been described for their use in treating spinal muscular atrophy or related disorders.

Thus, it is of the merit of the inventors to have provided new data showing that the pharmacological inhibition of ERK pathway, notably through the use of Selumetinib or related ERK inhibitors, could be an efficient treatment to alleviate SMA symptoms or related disorders associated to SMN deficiency resulting in loss of motor function in patients.

SUMMARY OF THE INVENTION

Therefore, it is an object of the present invention to provide methods for treating a neuromuscular disorder associated to a SMN deficiency resulting in loss of motor function, said method comprising administering a therapeutically efficient amount of an ERK inhibitor in a subject in need thereof.

Examples of neuromuscular disorders that can be treated with the method of the invention are preferably spinal muscular atrophy or other related neuromuscular disorders resulting from a genetic mutation in SMN1 gene.

ERK inhibitors for use in the method of the invention may be selected from MEK1/2 inhibitors, preferably from known MEK1/2 inhibitors with an IC50 of at least 1 μM, or less.

Typical examples of such known MEK1/2 inhibitors include, without limitation, selumetinib (also known as AZD6244), U0126, PD98059, PD0325901, AZD8330 (ARRY-42704), CI-1040 (PD184352), PD318088.

In a preferred embodiment, said ERK inhibitors are selected from Selumetinib or its derivatives or pharmaceutically acceptable salts.

In another embodiment, ERK inhibitors used in the method of treatment according to the invention are selected from the group consisting of nucleic acid molecules such siRNA, shRNA, and anti-sense oligonucleotides, said nucleic acid molecules being capable of reducing the expression of MEK1, MEK2, ERK1 and/or ERK2.

Preferably, said ERK inhibitors are administered orally to a subject in an amount effective to treat said neuromuscular disorders such as spinal muscular atrophy.

The invention further relates to a pharmaceutical composition comprising an ERK inhibitor in combination with another active principle ingredient for the treatment of spinal muscular atrophy and a pharmaceutically acceptable carrier. In one specific embodiment, said other active principle ingredient is selected from the group consisting siRNA, shRNA or antisense compounds directed against nucleic acid encoding a deficient SMN1 gene product resulting in loss of motor function.

DETAILED DESCRIPTION OF THE INVENTION

ERK Inhibitors for Use in the Treatment of Spinal Muscular Atrophies or Related Neuromuscular Disorders The invention more specifically relates to ERK inhibitors for use as a drug in the treatment of a neuromuscular disorder associated to a SMN deficiency resulting in loss of motor function.

As used herein, the term "treatment" refers to any methods appropriate to cure, ameliorate, stabilize and/or prevent a disease or one or more of the symptoms of such disease.

The term "ERK inhibitors" as used herein relates to compounds capable of fully or partially preventing, or reducing or inhibiting MEK ERK1/2 signaling activity.

Inhibition may be effective at the transcriptional level, for example by preventing or reducing or inhibiting mRNA synthesis of key members of MEK ERK1/2 signaling pathway, such as MEK1, MEK2, ERK1 or ERK2 mRNA, for example, mRNA encoding human MEK1 (NCBI reference NP-002746), human MEK2 (NCBI reference NP109587), human ERK1 (NCBI reference NP-002737) or human ERK2 (NCBI reference NP-620407).

As used herein the term "signalling pathway" or "signalling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The MEK ERK1/2 signalling pathway refers to the signalling pathway involving MEK and ERK (standing for Extracellular signals Regulated Kinase) serine/threonine selective protein kinases. Specific receptor kinases are activated through diverse extracellular stimuli and thus recruit the Ras family small G proteins, which lead to the sequential activation of Raf (MAPK kinase kinase), MEK (MAPK kinase) and ERK (MAPK). MAPK/ERK activity requires phosphorylation on both threonine (T185) and tyrosine (Y187).

In specific embodiments, the term "ERK inhibitor" is intended to refer to a substance that reduces, decreases and/or inhibits MEK ERK1/2 signaling activity as measured for example by the relative amount of phosphorylated ERK proteins or phosphorylated Elk1 protein.

Methods for detecting and measuring relative amount of phosphorylated ERK proteins or phosphorylated Elk1 protein are described in the Examples.

In a specific embodiment, said ERK inhibitors are compound inhibitor inhibiting MEK1, MEK2, ERK1 or ERK2 kinase activity. Specific inhibition may be measured as IC50 in a functional assay for MEK ERK1/2 signaling activity and the selected inhibitors may have an IC50 of 100 µM or less, 100 µM or less, 10 µM or less, 100 nM or less, 10 nM or less or 1 nM or less. Assays for measuring MEK1/2 kinase activity are commercially available.

Such inhibitors may thus be selected among small molecule, siRNA, shRNA, anti-sense DNA and the like.

In one embodiment, an ERK inhibitor for use according to the present invention is a small molecule. In another embodiment, said ERK inhibitor is selected from the group consisting of siRNA, shRNA, anti-sense oligonucleotides and related nucleic acids capable of inhibiting MEK1, MEK2, ERK1 and/or ERK2 gene expression.

Small Molecule ERK Inhibitors

In one embodiment, an ERK inhibitor for use in the treatment of spinal muscular atrophy or related disorders is a small molecule ERK inhibitor.

As used herein, the term "small molecule" refers to a low molecular weight organic compound which is not a polymer. Preferably, it has a molecular weight not upper than 800 Daltons so that it can rapidly diffuse across cell membranes so that they can reach intracellular sites of action.

A variety of a small molecule ERK inhibitors have been described in the Art, in particular MEK inhibitors such as MEK1 and/or MEK2 inhibitors, also referred as MEK1/2 inhibitors.

Such inhibitors include, but are not limited to, chromone and flavone type inhibitors. Other examples of suitable small molecule ERK inhibitors include, but are not limited to, PD 98059, a highly selective inhibitor of MEK1 and MEK2 with IC50 values of 4 µM and 50 µM respectively (Runden E et al., J Neurosci 1998, 18(18) 7296-305), PD0325901 (Pfizer), Selumetinib, a selective MEK inhibitor (AstraZeneca/Array BioPharma, also known as AZD6244), ARRY-438162 (Array BioPharma), PD198306 (Pfizer), PD0325901 (Pfizer), AZD8330 (AstraZeneca/Array Biopharma, also called ARRY-424704), PD184352 (Pfizer, also called CI-1040), PD 184161 (Pfizer), α-[Amino[(4-aminophenyl)thio]methylene]-2-(trifluoromethyl)benzeneacetonitrile (SL327), 1,4-Diamino-2,3-dicyano-1,4-bis(2-aminophenylthio)butadiene (DeSilva, D. R., et al. 1998. J. Immunol. 160, 4175. 165. Duncia, J. V., et al. 1998. Biorg. Med. Chem. Lett. 8, 2839. 166. Favata, M. F., et al. 1998. J. Biol. Chem. 273, 18623. 167. Ahn et al. (1999) Promega Notes. 71: 4), U0126 (Kohno & Pouyssegur (2003) Prog. Cell. Cyc. Res. 5: 219-224), GW 5074 (Santa Cruz Biotechnology), BAY 43-9006 (Bayer, Sorafenib), Ro 09-2210 (Roche, Williams et al., Biochemistry. 1998 Jun. 30; 37(26):9579-85), FR 1 80204 (Ohori, M. et al. (2005) Biochem. Biophys. Res. Comm. 336: 357-363), 3-(2-aminoethyl)-5-))4-ethoxyphenyl)methylene)-2,4-thiazolidinedione (PKI-ERK-005) (Chen, F. et al. (2006) Bioorg. Med. Chem. 16:6281-6288. 171. Hancock, C N. et al. (2005) J. Med. Chem. 48:

4586-4595), CAY10561 (CAS 933786-58-4; Cayman Chemical), GSK 120212, RDEA1 19 (Ardea Biosciences), XL518, and ARRY-704 (AstraZeneca).

Other ERK inhibitors and their synthesis methods have been described in U.S. Pat. No. 5,525,625, WO 98/43960, WO 99/01426, WO 00/41505, WO 00/42002, WO 00/42003, WO 00/41994, WO 00/42022; WO 00/42029, WO 00/68201; WO 01/68619; WO 02/06213: WO 03/077855 and WO 2005/23251.

Such ERK inhibitors further include, without limitation, a peptide inhibitor corresponding to the amino-terminal 13 amino acids of MEK1 (MPKKKPTPIQLNP (SEQ ID: 5 ))(Kohno & Pouyssegur (2003) Prog. Cell. Cyc. Res., 5:219-224). Peptide inhibitors may be obtained using usual chemical peptide synthesis or genetic engineering methods. Such peptide inhibitor may further be fused to additional peptide sequences, e.g. to linker, signal or leader sequences. A tag refers to a distinct amino acid sequence that can be used to detect or purify the peptide sequence but does not contribute to the essential function of ERK inhibition. Such peptide inhibitors may further be linked to internalization peptides or protein transduction domain such as the TAT transactivation domain of HIV, antennapedia, and transportan that can readily target molecules and small peptides across the plasma membrane into the cell (Schwarze et al., Science 1999 285(5433):1569-72).

A series of 3-cyano-4-(phenoxyanilo-)quinolines with MEK inhibitory activity has also been developed by Wyeth-Ayerst (Zhang N. et al., Bioorg Med. Chem. Lett., 2000, 10: 2825-2828). Several resorcyclic acid lactones having inhibitor activity toward MEK have been isolated from microbial extracts. For example, Ro 09-2210, isolated from fungal broth FC2506, and L-783,277, purified from organic extracts of *Phoma* sp. are competitive with ATP, and the MEK1 inhibition is reversible (Williams D. H. et al., Biochemistry, 1998, 37: 9579-9585; and Zhao A. et al., J. Antibiot., 1999, 52: 1086-1094).

Purvalanol, a cyclin-dependent kinase (CDK) inhibitor has also been shown to target ERK1 and ERK2 (Knockhaert M. et al., Oncogene, 2002, 21: 6413-6424).

Other ERK inhibitors that may be used in accordance with the present invention include those disclosed in U.S. patent publication 2003/0060469, U.S. patent publication 2004/0048861 and US patent publication 2004/0082631.

In a preferred embodiment, said ERK inhibitor is an inhibitor of MEK1 and/or MEK2 kinases selected from the group consisting of selumetinib, U0126, PD98059, PD0325901, AZD8330(ARRY-42704), CI-1040 (PD184352), PD318088.

Preferably, said ERK inhibitor is selected from the group consisting of semuletinib and its derivatives and pharmaceutically acceptable salts thereof.

Selumetinib, also known as AZD6244 is a MEK1/2 inhibitor having the following formula (I):

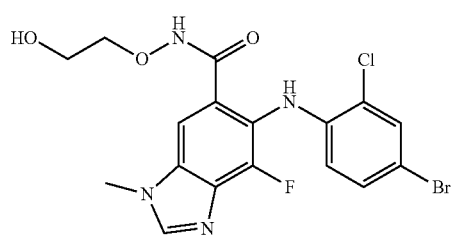

(I)

6-(4-bromo-2-chloroanilino)-7-fluoro-N-(2-hydroxyethoxy)-3-methylbenzimidazole-5-carboxamide Methods for synthesizing Selumetinib and other derivatives of Selumetinib or its pharmaceutically acceptable salts that can be used as ERK inhibitors according to the present invention have also been described in EP2275102 (see in particular Formula I as disclosed in EP2275102), WO 03/077855, and WO 03/077914.

siRNAs

Small inhibitory RNAs (siRNAs) can function as inhibitors of gene expression of a component of MEK/ERK1/2 signaling, thereby acting as ERK inhibitors. For example, gene expression of MEK1, MEK2, ERK1 or ERK2 can be reduced by contacting a subject or cell with a small double stranded RNA (dsRNA), or a vector or construct causing the production of a small double stranded RNA, such that said gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. Genes Dev. 1999 Dec. 15; 13(24):3191-7; Elbashir, S. M. et al Nature. 2001 May 24; 411(6836):494-8; Hannon, G J. Nature. 2002 Jul. 11; 418(6894):244-51); McManus, M T. et al. J Immunol 169, 5754-5760 (2002); Brummelkamp, T R. et al. Science. 2002 Apr. 19; 296 (5567):550-3; U.S. Pat. Nos. 6,573,099 and 6,506,559; and International Patent Publication Nos. WO 01/36646, WO 99/32619, and WO 01/68836). All means and methods which result in a decrease in MEK1, MEK2, ERK1 or ERK2 expression, in particular by taking advantage of MEK1, MEK2, ERK1 or ERK2-specific siRNAs (i.e. siRNAs that target specifically MEK1, MEK2, ERK1 or ERK2 mRNA) may be used in the present invention. Methods for generating and preparing siRNA(s) as well as method for inhibiting the expression of a target gene are also described for example in WO02/055693.

siRNAs or related nucleic acids useful as inhibitors of MEK1, MEK2, ERK1 or ERK2 gene expression, such as anti-sense oligonucleotides can be prepared by known methods. These include techniques for chemical synthesis such as, e.g., by solid phase phosphoramidite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone. Those modification includes the use of nucleosides with modified sugar moieties, including without limitation, 5'-vinyl, 5'-methyl(R or S), 4'-S, 2'-F, 2'-OCH$_3$ and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

Antisense oligonucleotides and siRNAs or related nucleic acids useful as inhibitors of MEK1, MEK2, ERK1 or ERK2 may be delivered in vivo alone or in association with a vector. In its broadest sense, a "vector" is any vehicle capable of facilitating the transfer of the antisense oligonucleotide or siRNA or related nucleic acids to the target cells, preferably those with deficient expression of SMN gene, such as muscular cells. Preferably, the vector transports the nucleic acid to cells with reduced degradation relative to the extent of degradation that would result in the absence of the vector. In general, the vectors useful in the invention include, but are not limited to, plasmids, phagemids, viruses, transposon-based vectors or other vehicles derived from viral or bacterial sources that have been manipulated by the insertion or incorporation of the antisense oligonucleotide or siRNA or related nucleic acid sequences. Viral vectors are a preferred type of vector and include, but are not limited to, nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Varmus, Harold; Coffin, John M.; Hughes, Stephen H., ed (1997). "Principles of Retroviral Vector Design". Retroviruses. Plainview, N.Y.: Cold Spring Harbor Laboratory Press. ISBN 0-87969-571-4.

Preferred viruses for certain applications are the adenoviruses and adeno-associated viruses or retroviral vectors such as lentiviruses, which are double-stranded DNA viruses that have already been approved for human use in gene therapy. Examples of such viral vectors includes vectors originated from retroviruses such as HIV (Human Immunodeficiency Virus), MLV (Murine Leukemia Virus), ASLV (Avian Sarcoma/Leukosis Virus), SNV (Spleen Necrosis Virus), RSV (Rous Sarcoma Virus), MMTV (Mouse Mammary Tumor Virus), etc, lentivirus, Adeno-associated viruses, and Herpes Simplex Virus, but are not limited to.

Theses viral vectors can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions.

Other vectors include plasmid vector, cosmid vector, bacterial artificial chromosome (BAC) vector, transposon-based vector. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or related nucleic acid sequence is under the control of a heterologous regulatory region, e.g., a heterologous promoter. The promoter can also be, e.g., a viral promoter, such as CMV promoter or any synthetic promoters.

siRNA can also be directly conjugated with a molecular entity designed to help targeted delivery. Examples of conjugates are lipophilic conjugates such as cholesterol, or aptamer-based conjugates. Cationic peptides and proteins are also used to form complexes with a negatively charged phosphate backbone of the siRNA.

Method of Treatment and Pharmaceutical Compositions

Another object of the invention relates to a method for treating spinal muscular atrophy or related neuromuscular disorders associated to a SMN deficiency resulting in loss of motor function, comprising administering a therapeutically effective amount of compound which is an ERK inhibitor as described above, to a subject in need thereof.

In one aspect, the invention relates to a method for treating spinal muscular atrophy comprising administering to a subject in need thereof a therapeutically effective amount of ERK inhibitor, such as Selumetinib or its derivatives or pharmaceutically acceptable salts as described above.

In another aspect, the invention provides ERK inhibitors as described above, which may be used for the preparation of a pharmaceutical composition for the treatment of spinal muscular atrophy or related neuromuscular disorders associated to a SMN deficiency resulting in loss of motor function.

ERK inhibitors may be administered in the form of a pharmaceutical composition, as defined below.

By a "therapeutically effective amount" is meant a sufficient amount of ERK inhibitor to treat and/or to prevent, reduce and/or alleviate one or more of the symptoms of spinal muscular atrophy or related neuromuscular disorders.

In one embodiment, said related neuromuscular disorder is selected from the group consisting of amyotrophic lateral sclerosis (also known as Charcot's disease or Lou Gehrig's disease or motoneuron's disease).

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Hence, the present invention also provides a pharmaceutical composition comprising an effective dose of ERK inhibitor, such as for example Selumetinib or its derivatives or pharmaceutically acceptable salts, for use according to the invention.

Any therapeutic agent of the invention may be combined with pharmaceutically acceptable excipients, and optionally sustained-release matrices, such as biodegradable polymers, to form therapeutic compositions.

The therapeutic agent, i.e. the ERK inhibitors, may be combined with other active ingredients, for example siRNA, shRNA or antisense compounds directed against nucleic acid encoding a deficient SMN1 gene product resulting in loss of motor function.

In one specific embodiment, such ERK inhibitors may be combined with compositions for modulating splicing of SMN2 mRNA, including without limitation, those disclosed in WO2010/148249.

In another specific embodiment, the ERK inhibitors may be combined with c-Jun NH2-terminal kinase (INK) inhibitor, such as those described in WO 2010/151638.

"Pharmaceutically" or "pharmaceutically acceptable" refers to molecular entities and compositions that do not produce an adverse, allergic or other reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Pharmaceutically acceptable carriers include any and all solvents (such as phosphate buffered saline buffers, water, saline), dispersion media, coatings, antibacterial and antifungal agents, isotonic and absorption delaying agents and the like. Formulations are described for example in Remington's Pharmaceutical Science (Martin E. W. (1995) Easton Pa., Mack Publishing Company, 19$^{th}$ ed.)

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Method of Screening Agents for Treating Spinal Muscular Atrophy or Related Disorders A role for MEK ERK1/2 pathway in neuromuscular disorders associated to SMN deficiencies has neither been described nor proposed in the prior art. Therefore, it is most surprising that by inhibiting MEK ERK1/2 signaling pathway, SMN2 gene expression is significantly increased. Accordingly, the present invention provides method for screening agents for treating spinal muscular atrophy or related disorders, said method comprising screening ERK inhibitors.

In one specific embodiment, the invention provides methods for screening agents for treating spinal muscular atrophy or related disorders comprising (i) selecting compounds that binds to MEK1 or MEK2 kinases with high affinity in a primary binding assay and (ii) selecting from those binding compounds, the compounds that specifically inhibit MEK ERK1/2 signaling in a secondary functional assay.

The screening methods of the invention generally comprise a first primary binding screening assay, generally carried as a high throughput screening assay, designed to identify compounds that bind with a high affinity to MEK1 or MEK2 protein or ERK1 or ERK2 protein. In one embodiment, "high affinity" refers to compounds that binds to the target protein with a dissociation constant $K_D$ of 100 µM or less, 10 µM or less, 1 µM or less, 100 nM or less, 10 nM or less, or 1 nM or less. $K_D$ affinity can be measured for example using surface Plasmon resonance, such as Biacore® assay (Biacore Life Sciences).

Compounds may be tested from large libraries of small molecules, natural products, peptides, peptidomimetics, polypeptides, proteins or a combination thereof or any appropriate compound libraries for drug discovery. Synthetic compound libraries are commercially available from Maybridge Chemical Co (Trevillet, Cornwall, UK), Comgenex (Princeton, N.J.), Brandon Associates (Merrimack, N.H.), and Microsource (New Milford, Conn.). Compounds may also be screened from derivatives of known ERK inhibitors.

Examples of such primary binding assays for identifying MEK1 or MEK2 binders include without limitations the FRET-assays or TR-FRETs (in "A homogeneous time resolved fluorescence method for drug discovery" in: High Throughput screening: the discovery of bioactive substances. Kolb (1997) J. Devlin. NY, Marcel Dekker 345-360).

Once hit molecules or binding compounds have been selected from the primary screening assay, they are generally subject to a secondary functional assay for testing specific inhibition of MEK ERK1/2 signaling pathways. In one other embodiments, such secondary functional assay is used as the primary assay for direct screening of compound inhibitors.

As used herein, the term "specific inhibition" refers to an inhibition that is dependent upon the presence of an activator of said MEK ERK1/2 signaling pathway, preferably dose-dependent. Intensity of the inhibition can be referred as $IC_{50}$, i.e., the concentration of the inhibitors required to obtain 50% of inhibition in a determined assay. In one embodiment, specific inhibitors have an $IC_{50}$ of 100 µM or less, 10 µM or less, 1 µM or less, 100 nM or less, 10 nM or less or 1 nM or less, as measured in the secondary functional assay.

The secondary screening may be for example a biochemical assay or cellular-based assay for detecting MEK ERK1/2 signaling inhibition.

Biochemical assay may for example include a substrate for MEK1 and MEK2 kinases (for example a recombinant ERK1 or ERK2 protein and purified MEK1 or MEK2 kinase or an enzyme with related activity) and means for detecting the phosphorylated substrate (P-ERK for example). Such means may be specific antibody for phosphorylated substrate. The assay consists in measuring the amount of phosphorylated substrate after incubation with the purified enzyme in the absence or presence of the tested compound. Inhibition is detected as a significant and dose-dependent decrease of phosphorylated substrate.

Cellular-based assay includes assays which enable the determination of the activation profile of known molecular targets of the MEK ERK1/2 pathway, including, without limitation, the transcription factor Elk1 as described in the Examples below.

Compounds that exhibit one or more inhibition properties, the "lead" molecules, may then be chemically modified, for example for improving their binding properties, their pharmacokinetic and pharmacodynamic properties (e.g. solubility and ADME properties).

Using the assays described in the present invention and the art related to known ERK inhibitors, the skilled person is thus able to identify novel ERK inhibitors, for use according to the present invention.

In the following, the invention will be illustrated by means of the following examples as well as the figures.

FIGURE LEGENDS

FIG. 1:
A. Smn Promoter site 1 sequence (SEQ ID NO: 6)
B. Smn Promoter site 2 sequence (SEQ ID NO: 7)
C and D. Western blot analysis and quantification of Elk-1 protein phosphorylation in the ventral lumbar spinal cord of vehicle- and NMDA-treated control mice at 6 days of age, of vehicle SMA-like mice at 2 days of age and NMDA-treated SMA-like mice at 6 days of age (n=2). Error bars indicate SEM. (*, $p<0.05$).
E and F. ChIP analysis of Phospho-Elk-1 in the ventral lumbar spinal cord of vehicle- and NMDA-treated control mice at 6 days of age, of vehicle SMA-like mice at 2 days of age and NMDA-treated SMA-like mice at 6 days of age (n=9). Quantitative real time PCR was performed to detect SMN2 promoter site 1 (E) and site 2 (F). Error bars indicate SEM. (*, $p<0.05$; , $p<0.01$; *, $p<0.001$).
G and H. ChIP analysis of Phospho-CREB in the ventral lumbar spinal cord of vehicle- and NMDA-treated control mice at 6 days of age, of vehicle SMA-like mice at 2 days of age and NMDA-treated SMA-like mice at 6 days of age (n=9). Quantitative real time PCR was performed to detect SMN2 promoter site 1 (G) and site 2 (H). Error bars indicate SEM. (, $p<0.01$; *, $p<0.001$).
I and J. ChIP analysis of Histone H3 acetylation in the ventral lumbar spinal cord of vehicle- and NMDA-treated control mice at 6 days of age, of vehicle SMA-like mice at 2 days of age and NMDA-treated SMA-like mice at 6 days of age (n=9). Quantitative real time PCR was performed to detect SMN2 promoter site 1 (1) and site 2 (J). Error bars indicate SEM. (*, $p<0.05$; , $p<0.01$; *, $p<0.001$).
K and L. ChIP analysis of Histone H4 acetylation in the ventral lumbar spinal cord of vehicle- and NMDA-treated control mice at 6 days of age, of vehicle SMA-like mice at 2 days of age and NMDA-treated SMA-like mice at 6 days of age (n=9). Quantitative real time PCR was performed to detect SMN2 promoter site 1 (K) and site 2 (L). Error bars indicate SEM. (*, $p<0.05$; *** , $p<0.001$).

Figure 2:
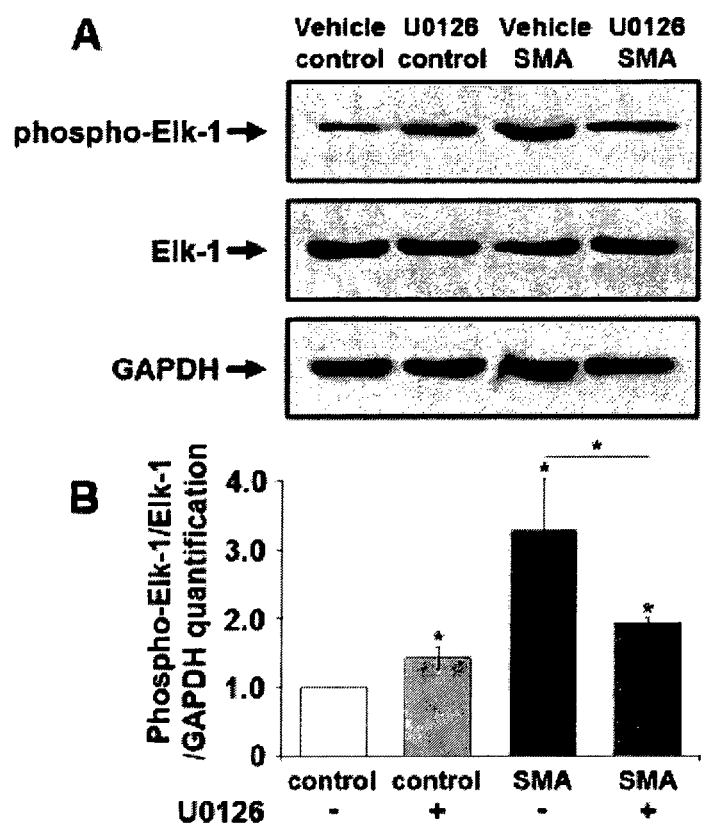
Figure 2:
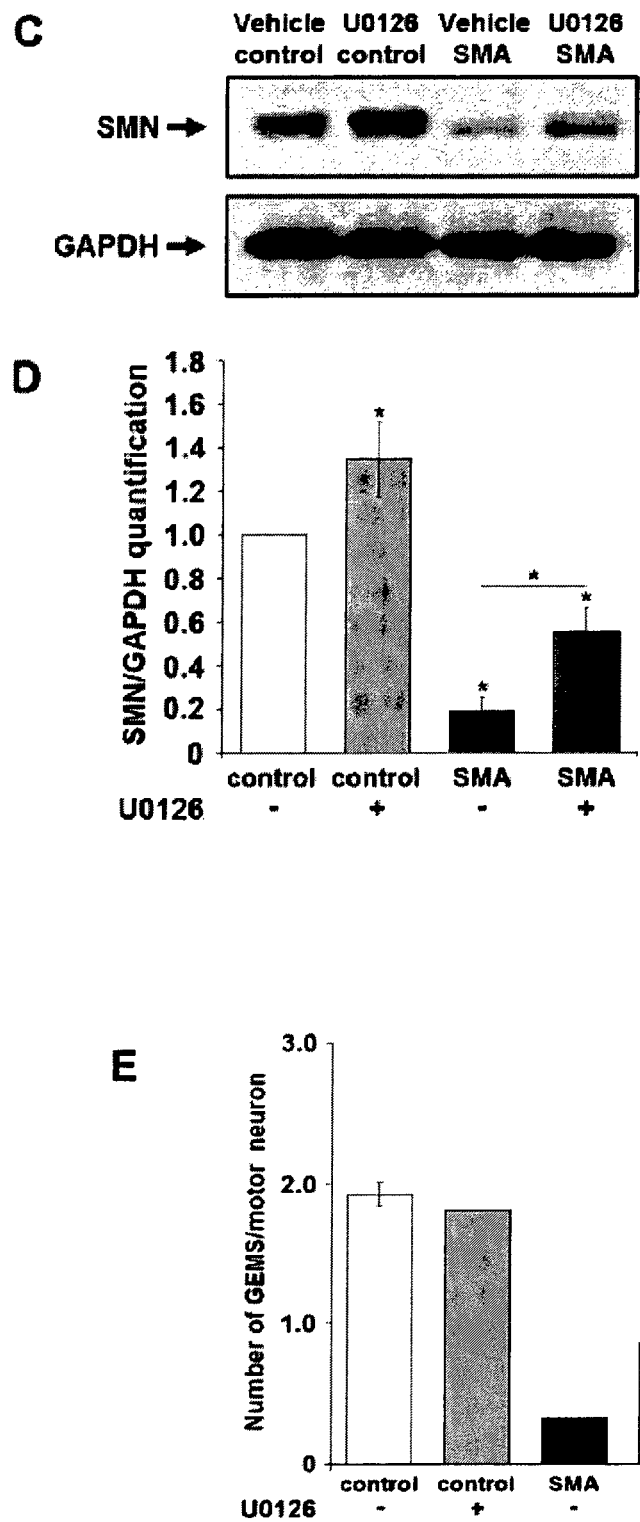
Figure 2:
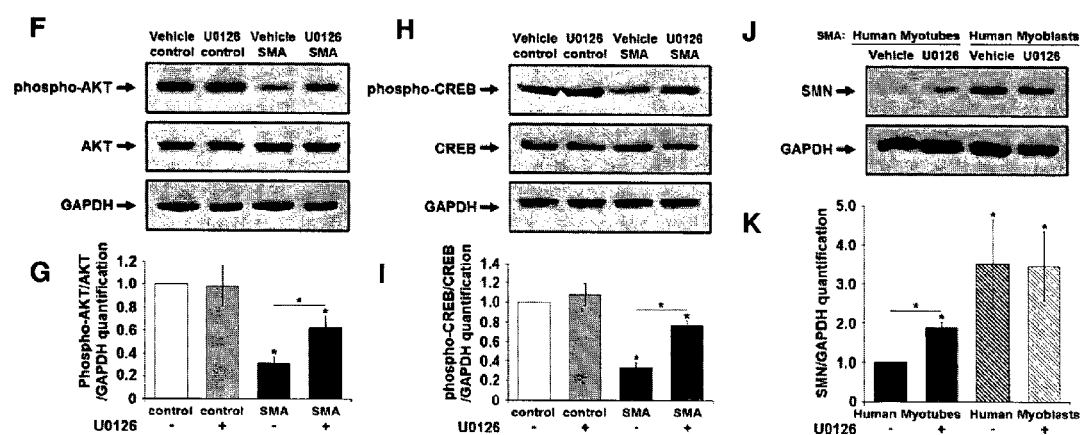

FIG. 2:
A and B. Western blot analysis and quantification of Elk-1 protein phosphorylation in the ventral lumbar spinal cord of vehicle- and NMDA-treated control mice at 6 days of age, of vehicle SMA-like mice at 2 days of age and U0126-treated SMA-like mice at 6 days of age (n=3). Error bars indicate SEM. (*, $p<0.05$).
C and D. Western blot analysis and quantification of SMN protein expression in the ventral lumbar spinal cord of vehicle- and NMDA-treated control mice at 6 days of age, vehicle SMA-like mice at 2 days of age and U0126-treated SMA-like mice at 6 days of age (n=2). Error bars indicate SEM. (*, $p<0.05$).

E. Quantitative analysis of the number of GEMS per motor neuron in the ventral lumbar spinal cord of vehicle- and NMDA-treated control mice at 6 days of age, of vehicle SMA-like mice at 2 days of age and U0126-treated SMA-like mice at 6 days of age (n=2).
F and G. Western blot analysis and quantification of AKT protein phosphorylation in the ventral lumbar spinal cord of vehicle- and NMDA-treated control mice at 6 days of age, of vehicle SMA-like mice at 2 days of age and U0126-treated SMA-like mice at 6 days of age (n=3). Error bars indicate SEM. (*, $p<0.05$).
H and I. Western blot analysis and quantification of CREB protein phosphorylation in the ventral lumbar spinal cord of vehicle- and NMDA-treated control mice at 6 days of age, of vehicle SMA-like mice at 2 days of age and U0126-treated SMA-like mice at 6 days of age (n=3). Error bars indicate SEM. (*, $p<0.05$).
J and K. Western blot analysis and quantification of SMN protein expression in vehicle and U0126-treated human SMA cultured myotubes and myoblasts (n=2). Error bars indicate SEM. (*, $p<0.05$).

Figure 3:
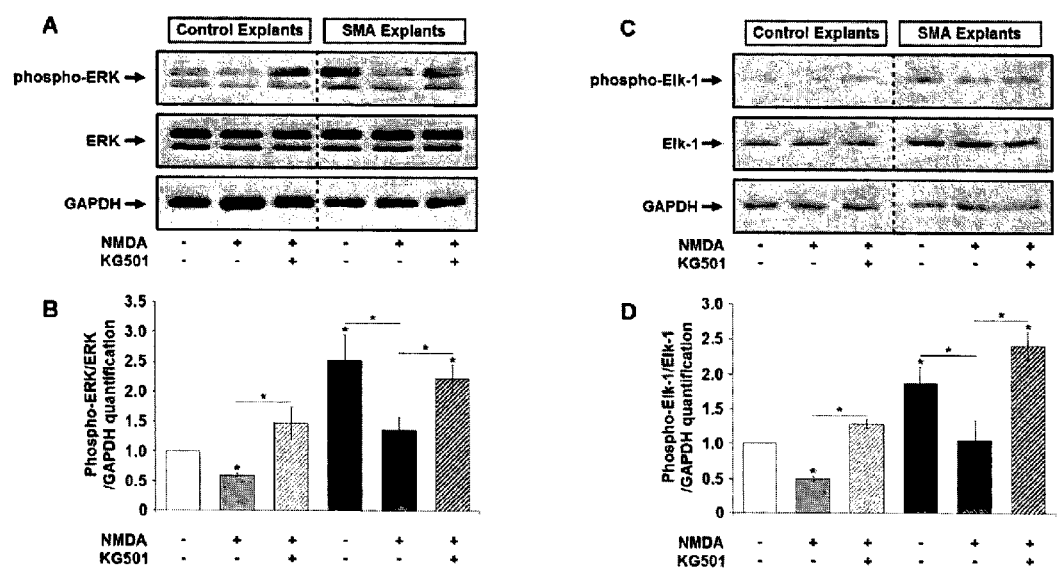
Figure 3:
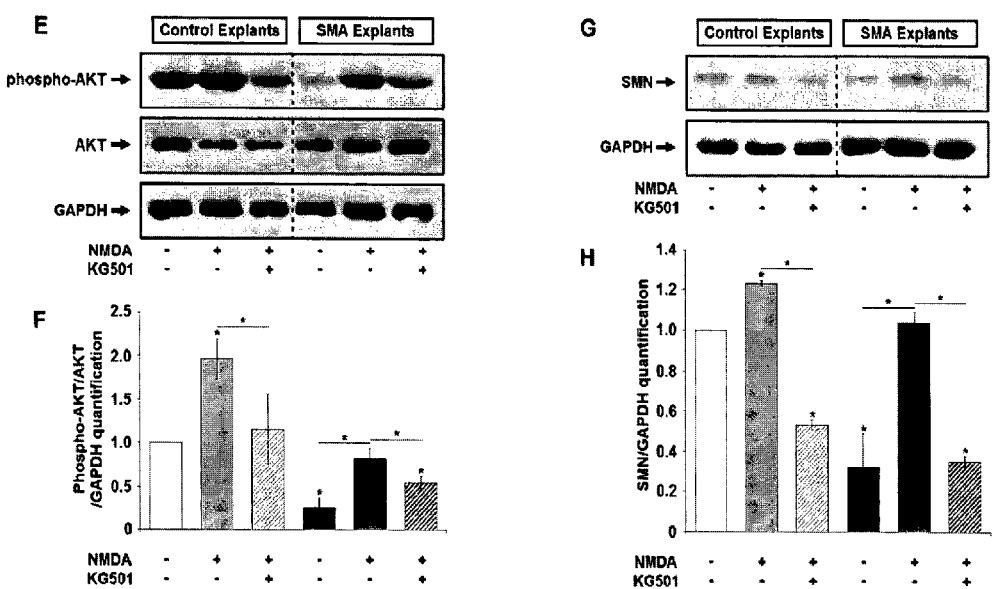

FIG. 3:
A and B. Western blot analysis and quantification of ERK protein phosphorylation in the control and SMA spinal cord explants in presence or not of NMDA and of the CREB inhibitor KG501 (n=2). Error bars indicate SEM. (*, $p<0.05$).
C and D. Western blot analysis and quantification of Elk-1 protein phosphorylation in the control and SMA spinal cord explants in presence or not of NMDA and of the CREB inhibitor KG501 (n=2). Error bars indicate SEM. (*, $p<0.05$).
E and F. Western blot analysis and quantification of AKT protein phosphorylation in the control and SMA spinal cord explants in presence or not of NMDA and of the CREB inhibitor KG501 (n=3). Error bars indicate SEM. (*, $p<0.05$).
G and H. Western blot analysis and quantification of SMN protein expression in the control and SMA spinal cord explants in presence or not of NMDA and of the CREB inhibitor KG501 (n=2). Error bars indicate SEM. (*, $p<0.05$).

Figure 4:
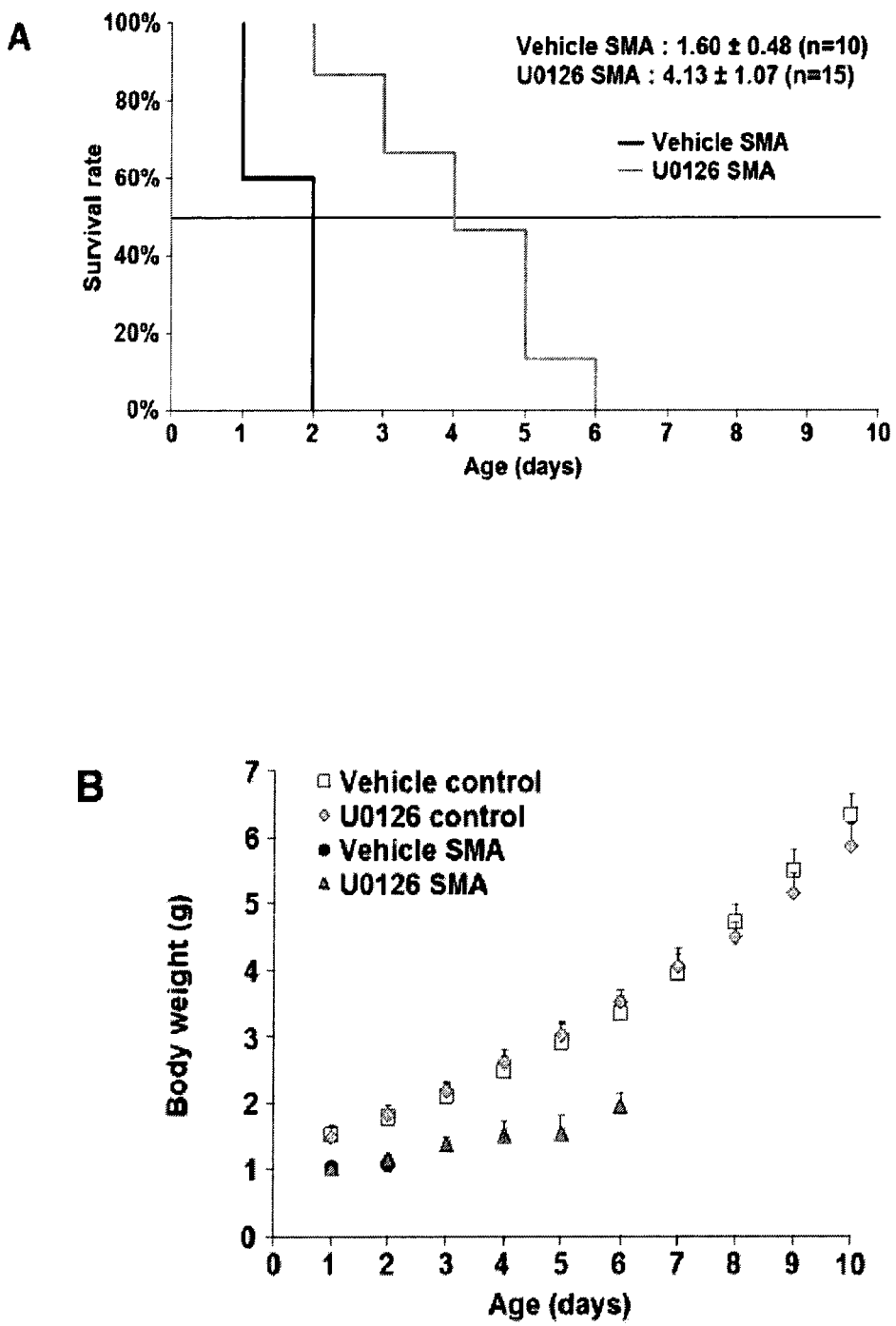
Figure 4:
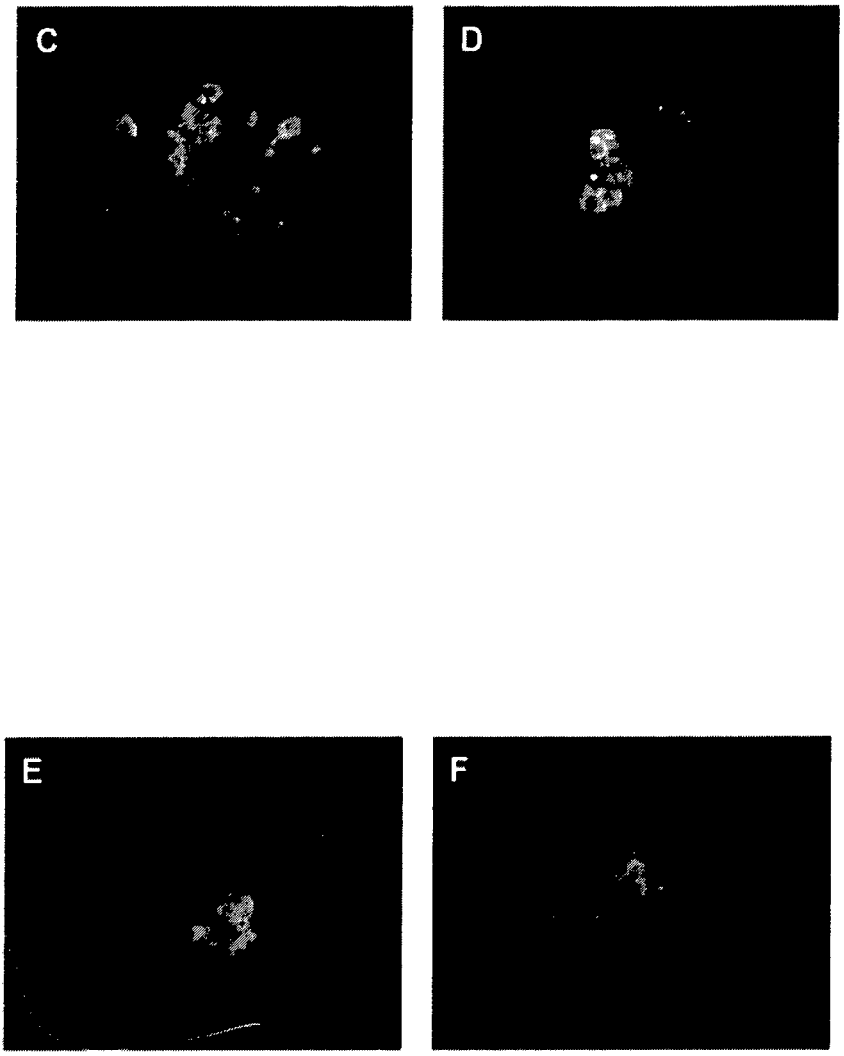
Figure 4:
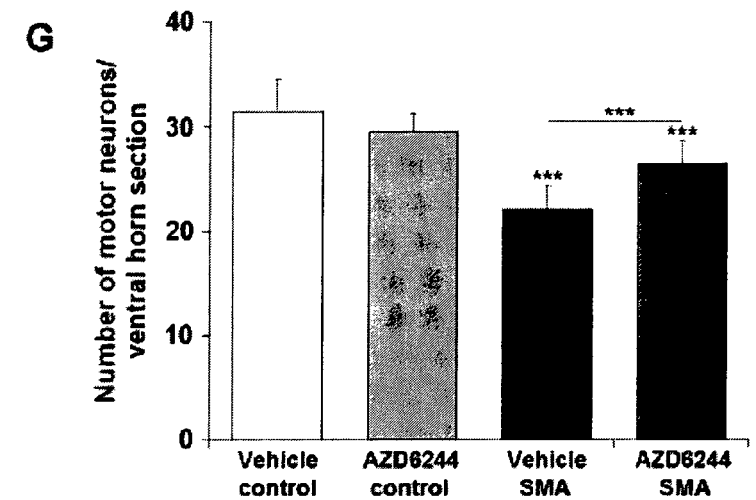
Figure 4:
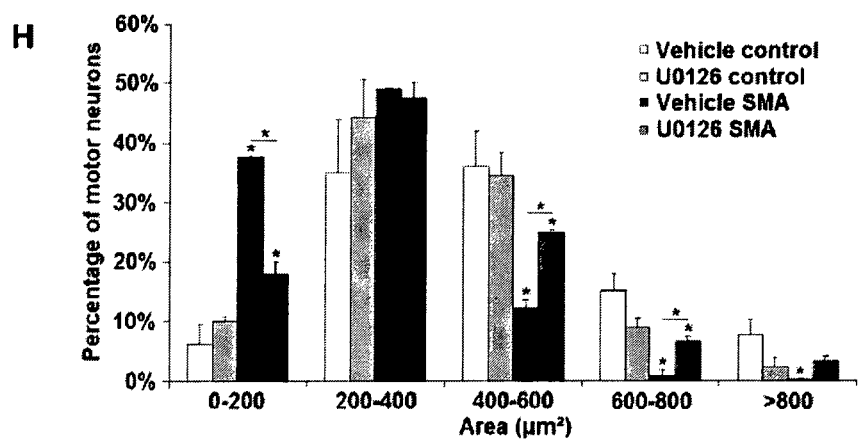
Figure 4:
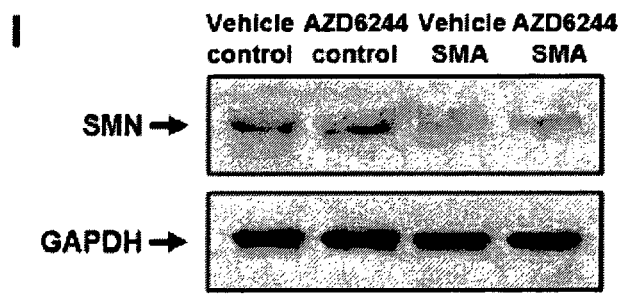
Figure 4:
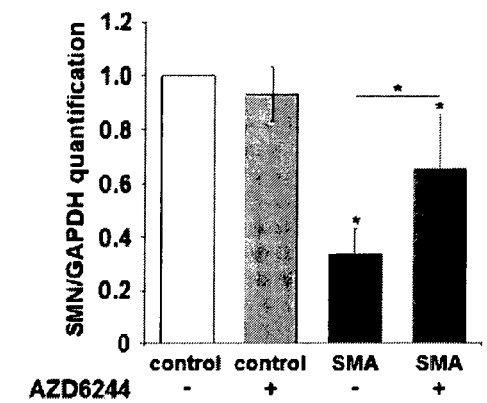
Figure 4:
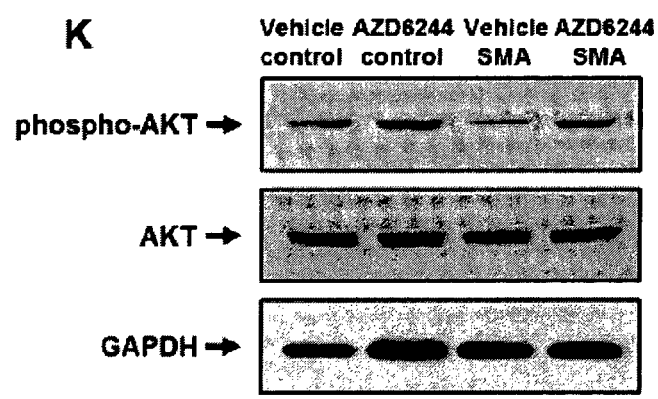
Figure 4:
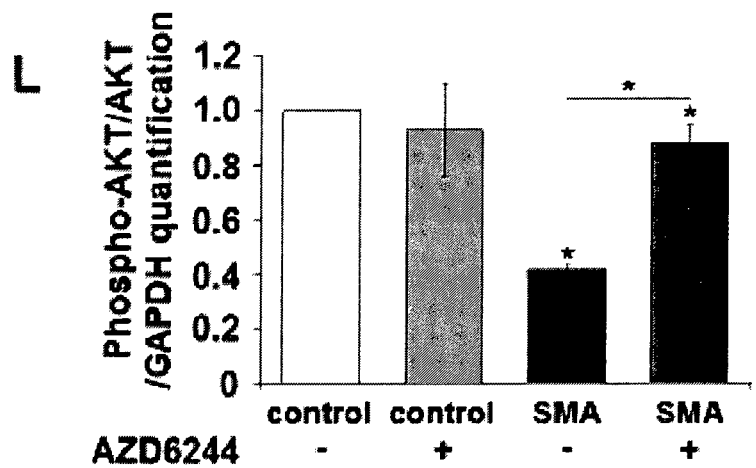
Figure 4:
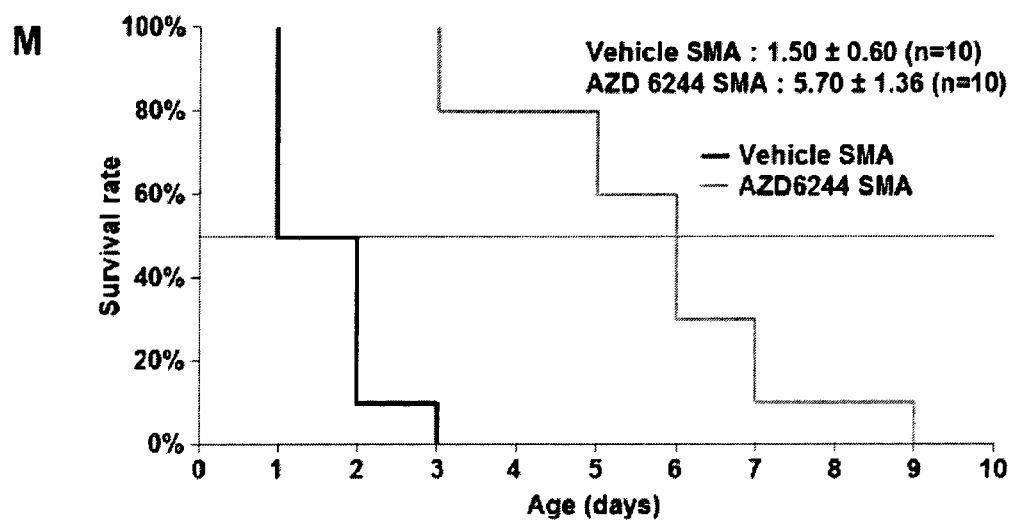
Figure 4:
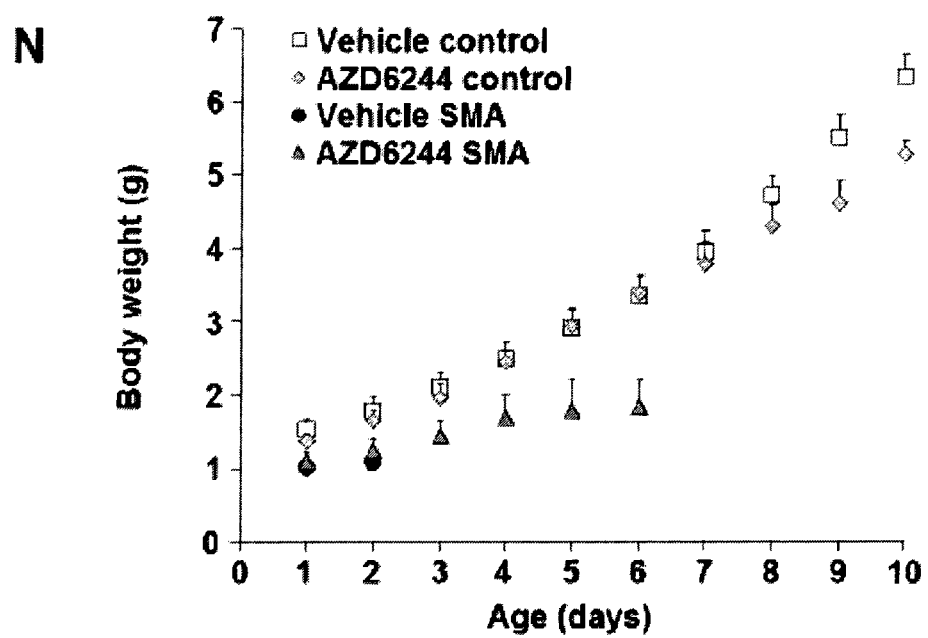

FIG. 4:
A. Life span of U0126-treated (n=15) compared to vehicle-treated SMA-like mice (n=10).
B. Weight curve in U0126-treated (n=15) and vehicle-treated SMA-like mice (n=10) compared to U0126-treated (n=15) and vehicle-treated control (n=15).
C-F. Immunodetection of ChAT-positive motor-neurons in the lumbar spinal cord (L1-L5) of 6 days of age vehicle- (C) and U0126-treated control mice (D), and 2 days of age vehicle- (E) and 6 days of age U0126-treated SMA-like mice (F).
G and H. Quantitative analysis of the number (G) and the cell body area (H) of motor neurons per ventral horn in the ventral lumbar spinal cord of vehicle- and U0126-treated control mice at 6 days of age, of vehicle SMA-like mice at 2 days of age and U0126-treated SMA-like mice at 6 days of age (n=3). Error bars indicate SEM. (*, $p<0.05$).
I and J. Western blot analysis and quantification of SMN protein expression in the ventral lumbar spinal cord of vehicle- and AZD6244-treated control mice at 6 days of age, vehicle SMA-like mice at 2 days of age and AZD6244-treated SMA-like mice at 6 days of age (n=3). Error bars indicate SEM. (*, $p<0.05$).
K and L. Western blot analysis and quantification of AKT protein phosphorylation in the ventral lumbar spinal cord of vehicle- and AZD6244-treated control mice at 6 days of age, of vehicle SMA-like mice at 2 days of age and AZD6244-treated SMA-like mice at 6 days of age (n=3). Error bars indicate SEM. (*, p<0.05).

M. Life span of AZD6244-treated (n=10) compared to vehicle-treated SMA-like mice (n=10).

N. Weight curve in AZD6244-treated (n=10) and vehicle-treated SMA-like mice (n=10) compared to AZD6244-treated (n=10) and vehicle-treated control (n=10).

EXAMPLES

Materials and Methods
Mice and Treatments

The knockout-transgenic SMA-like mice ($Smn^{-/-}$, $SMN2^{+/+}$) were purchased from the Jackson Laboratory (Bar Harbor, Me.) and genotyped as previously described[15]. Vehicle-treated group, NMDA-treated group, U0126-treated group and AZD6244-treated group of type 1 SMA-like mice were randomly constituted in a blind systematic manner to minimize bias. The control mice were heterozygous knock-out for Smn with the human SMN2 transgene ($Smn^{-/+}$, to $SMN2^{+/+}$).

In order to evaluate phospho-Elk-1 and phospho-CREB role on Smn2 promoter, P1 neonatal control and SMA-like mice, were either injected intrathecally with 5 pmol of N-methyl-D-aspartic Acid 100 μM (NMDA, Sigma, Saint Quentin Fallavier, France) in 0.5 μl/g of 0.9% NaCl dyed in blue Evans per gram. These mice were compared to control and SMA-like mice injected from P1 with 0.5 μl/g of 0.9% NaCl dyed in blue Evans.

In order to evaluate the benefits of phospho-ERK inhibition, P1 neonatal control and type 1 SMA-like mice were injected either intrathecally with 0.5 pmol of 1,4-Diamino-2,3-dicyano-1,4-bis(o-aminophenylmercapto)butadiene monoethanolate 10 μM (U0126, Sigma, Saint Quentin Fallavier, France) in 0.5 μl/g of 0.9% NaCl 1% DMSO dyed in blue Evans per gram, or per os with 0.5 pmol of Selumetinib 10 μM (AZD6244, Selleck chemicals, Houston, Tex.) in 2 μl/g of 0.9% NaCl 1% DMSO. These mice were compared to control and SMA-like mice either injected from P1 with 0.5 μl/g of 0.9% NaCl 1% DMSO dyed in blue Evans or orally treated with 2 μl/g of 0.9% NaCl 1% DMSO. Body weight and life span recordings were performed every day until the death of the animal. The animals were considered as dead when mice were no longer able to stand up 20 sec after having been placed on their sides.

The care and treatment of animals followed the national authority (Ministère de la Recherche et de la Technologie, France) guidelines for the detention, use and the ethical treatment of laboratory animals.

Mouse Cell Cultures and Treatments

Co-cultures of spinal cord explants (around 1 mm³) and muscle cells were performed as described by Kobayashi et al.[25] with the following modifications. Spinal cord explants were obtained from control and severe SMA embryonic mice. Explants from the whole transverse slices of 10.5 days-old mice embryo spinal cords including dorsal root ganglia (DRG) were placed on the muscle monolayer. DRG are essential to ensure a good innervation ratio[25]. The muscle culture was established through the differentiation of the wild-type muscle cell line C2C12. Myoblast cells were cultured on 35 mm petri dish at 37° C. in 5% $CO_2$ in Dulbecco's Modified Eagle's Medium (DMEM) supplemented with 2 mM glutamine, 20% fetal bovin serum, 2% penicillin/streptomycin (5000 U). All the culture medium reagents were purchased from Invitrogen Life Technologies (Cergy-Pontoise, France). Confluent myoblasts were differentiated into myotubes in DMEM supplemented with 2 mM glutamine, 5% horse serum, 2% penicillin/streptomycin (5000 U) (Differentiation medium, DM). After 5-7 days in DM, spinal cord explants were added on the cultured contracting muscle cells. After co-culture with spinal cord, the culture was kept in DM. All co-cultures were fed three times a week and examined daily by phase-contrast inverted microscopy to check the appearance of the innervation.

Stimulation of the NMDARs was achieved by exposing cells to 100 μM NMDA, as previously described[14]. To evaluate the CREB dependency, KG-501 (10 μM, Sigma) was added to the culture. After 5 days of treatment, explants were mechanically removed from the muscle layer, and proteins were purified and analyzed by western blot as described below.

Human Primary Culture of Myogenic Precursor Cells from SMA Patients Biopsies

Muscle biopsies were obtained from the BTR (Bank of Tissues for Research, a partner in the EU network Euro-BioBank) in accordance with European recommendations and French legislation. Satellite cells were isolated from biopsies and cultivated as described previously[26] in growth medium consisting of 1 vol 199 Medium/4 vol DMEM (Invitrogen Life Technologies) supplemented with 20% fetal bovin serum (Invitrogen Life Technologies), 2.5 ng/ml hepatocyte growth factor (HGF) (Invitrogen Life Technologies), and 50 μg/ml Gentamycin (Invitrogen Life Technologies). Further expansion was made in growth medium without HGF. The myogenic purity of the populations was monitored by immunocytochemistry using desmin as a marker. Differentiation was induced at confluence by replacing the growth medium with DMEM supplemented with 4% horse serum and 50 μg/ml of gentamycin (Sigma). Specific blockade of MEK phosphorylation was achieved during 5 days using 10 μM of U0126 (Sigma).

Histological and Immunohistochemical Analysis

Spinal cords were dissected and incubated overnight in 4% PFA PBS solution, and washed twice for 2 h with PBS. The lumbar spinal cords (L1 to L5) were embedded in 4% Agarose solution in sterilized water for 30 min at 4° C. 50 μm sections were then performed using a vibratome on the whole length of the sample. One out of every five sections was processed for immunohistochemical analysis. Tissue sections were incubated for 1 h at room temperature in a blocking solution (10% normal donkey serum with 0.5% Triton X-100 and 1% Tween in Tris Buffer Solution (TBS)). Motor neuron and Gemini of coiled bodies immunodetection were performed using a polyclonal goat anti-choline acetyl-transferase (ChAT) primary antibody (1:400; Chemicon, Inc., Temecula, Calif.) and a monoclonal mouse anti-SMN primary antibody (1:200; BD Transduction Laboratories, Lexington, Ky.) for 4 days at 4° C. in 3.5% donkey serum with 0.1% Tween TBS. Sections were washed between each subsequent step with 0.1% Tween in TBS. Sections were subsequently incubated with polyclonal $C_y$™3 conjugated Donkey anti-Goat antibodies (1:400; Jackson ImmunoResearch, West Grove, Pa.) and polyclonal Cy™2-conjugated Donkey anti-Mouse antibodies (1:400; Jackson ImmunoResearch) for 1 h at room temperature in 3.5% donkey serum with 0.1% Tween TBS. The sections were washed three times for 10 min in 0.1% Tween TBS and mounted in Fluoromount G™ (SouthernBiotech, Birmingham, Ala.) mounting medium. The staining specificity was checked in control incubations performed in the absence of the primary antibody.

All counts were performed using ImageJ software v1.37 (National Institutes of Health, Bethesda, Md.). Color images were tinted using Image Pro-Plus software, where identical brightness, contrast, and color balance adjustments were applied to all groups.

Microscopy

All immunofluorescence images were collected with a CCD camera (QImaging Retiga 2000R Fast, Cooled Mono 12 bit) mounted on Olympus microscope (BX51) using the Image Pro-Plus v6.0 software (MediaCybernetics Inc., Bethesda, Md.) with ×40 (4× Olympus objective UPlan FL N 0.13), 100 (10× Olympus objective UPlan FL N 0.3), 200 (20× Olympus objective FL N 0.5), 400 (40× Olympus objective UPlan FL N 0.75), 600 (60× Olympus objective UPlanS Apo 1.35 oil) and 1000 (100× Olympus objective UPlanS Apo 1.4 oil) magnifications.

Protein and Western Blot Analysis

Ventral lumbar spinal cord samples (2 to 5 mg) were homogenized in 100 µl/5 mg tissues of ice-cold RIPA buffer (50 mM Tris HCl pH=8.0, 150 mM NaCl, 0.1% SDS, 0.5% sodium deoxycholate, 1% NP40, 5 mM EDTA pH 8.0, 2 mM PMSF (phenyl-methylsulfonyl fluoride, Sigma-Aldrich), 50 µg/ml leupeptin, 50 µg/ml pepstatin A and 50 µg/ml aprotinin). Protein concentration of the clarified homogenates (4° C., 15 min, 13,500 rev·min-1) was determined on all samples using the Bradford protein assay (Biorad Laboratories, CA). 10 µg protein samples for SMN analysis and 30 µg samples for other analysis of each homogenate were submitted to 12.5% SDS-PAGE electrophoresis (1.5 M Tris pH 8.3, 12.5% Acrylamide, 0.07% Bis, 0.1% SDS, 0.05% APS, 0.06% TEMED). The separated proteins were transferred on PVDF membranes (Biorad) according to Towbin et al.[27]. Equal loading of samples was checked by Ponceau dye staining of the transferred gels. Western blot analysis was performed on membranes overnight at 4° C. in 4% BSA, 0.05% TWEEN 20, TBS pH 7.4. Each of the following primary antibodies, including monoclonal mouse anti-SMN (1:5,000; Santa Cruz Biotechnology, Inc.), polyclonal rabbit anti-Ser473 phospho-AKT (1:1000; Cell signaling Technology, Inc, Boston, Mass.), polyclonal rabbit anti phospho-ERK1/2 (1:500; Cell Signaling, Inc.), polyclonal rabbit anti-Ser133 phospho-CREB (1:1,000; Millipore), monoclonal mouse anti-Ser183 phospho-Elk-1 (1:1,000; Santa Cruz Biotechnology, Inc) was incubated overnight at 4° C. in the above blocking medium. Membranes were rinsed in 0.1% TWEEN 20 in TBS for 3×10 min at room temperature and then incubated in horseradish peroxydase-conjugated Goat secondary antibody directed against Mouse Immunoglobulins (1:5,000; Biorad Laboratories, CA) and in horseradish peroxydase-conjugated Goat secondary antibody directed against Rabbit Immunoglobulins (1:10,000; Jackson ImmunoResearch) in 0.1% TWEEN 20 in TBS for 1 h at room temperature. Bound antibody complexes were developed using the ECL system (Amersham Biotech., Saclay, France) and exposed to hyperfilm ECL-plus X ray film (Amersham Biotech.).

In some instances, membranes were stripped after immunoblotting with phospho-AKT, phospho-ERK1/2, phospho-CREB and phospho-Elk-1 by incubation in stripping buffer (100 mM β-mercaptoethanol, 2% SDS, 62.5 mM Tris-HCl, pH 6.7) for 30 min at 55° C. with agitation, and membranes were then blocked and reprobed with polyclonal rabbit anti-AKT (1:1,000; Cell Signaling, Inc.), polyclonal rabbit anti-ERK1/2 (1:500; Cell Signaling, Inc.), polyclonal rabbit anti-CREB (1:1,000; Millipore), monoclonal mouse anti-Elk-1 (1:1,000; Santa Cruz Biotechnology, Inc.) and monoclonal mouse anti-glyceraldehyde-3-phosphate dehydrogenase antibody (GAPDH) (1:5,000; Chemicon). Films were quantified with ImageJ v1.37 (National Institutes of Health, Bethesda, Md.) and the results reported as means±SEM.

Chromatin Immunoprecipitation

Ventral lumbar Spinal Cord samples were chopped into small pieces with a scalpel and were fixed for 15 min with 1% formaldehyde. Tissues were washed 3 times in cold PBS containing protease inhibitors (2 mM PMSF, 50 µg/ml leupeptin, 50 µg/ml pepstatin A and 50 µg/ml aprotinin) and collected by centrifugation. Cell pellet were resuspended and incubated on ice for 10 min in 300 µl of lysis buffer (5 mM piperazine-N,N'-bis(2-ethanosulfonic acid) (PIPES) pH 8.0, 85 mM KCL, 0.5% NP-40) and protease inhibitors. Cells were pelleted by centrifugation and resuspended in 300 µl of 1% SDS, 10 mM EDTA and 50 mM Tris-HCL (pH 8.0) containing protease inhibitors. After incubation on ice for 10 min, cells were sonicated 6 times for 30 sec using Bioruptor (Diagenode, Philadelphia, Pa.). Lysates were cleared by centrifugation and DNA concentration was determined using a nanodrop spectrophotometer. ChIP-Adembeads (Ademtech SA, Pessac, France) were incubated for 15 min at room temperature with blocking buffer on a rotating wheel. Beads were resuspended in 125 µl of ChIP Dilution buffer (0.01% SDS, 1% Triton X100, 1.2 mM EDTA, 16.7 mM Tris-HCl (pH 8.1)), and after a 1 h incubation, equal amounts of DNA diluted 10 times in dilution buffer were added. DNA was incubated overnight at 4° C. on a rotating wheel with 1 µg of the following antibodies: polyclonal rabbit anti-Ser133 phospho-CREB (Millipore), monoclonal mouse anti-Ser183 phospho-Elk-1 (Santa Cruz Biotechnology, Inc), polyclonal rabbit anti-acetyl-Histone H3 Lys9 (Millipore) and polyclonal rabbit-acetyl-Histone H4 Lys 8 (Upstate Biotechnology, Inc., Lake Placid, N.Y.). Beads were washed sequentially in TSE (0.1% SDS, 1% Triton X100, 2 mM EDTA, 20 mM Tris-HCl (pH 8.1) with 150 mM NaCl, TSE with 500 mM NaCl, buffer A (0.25 M LiCl, 1% NP-40, 1% deoxycholate, 1 mM EDTA, 10 mM Tris-Hcl (pH 8.1), and 2 times with tris-EDTA and then eluted with 200 µl 1% SDS and 0.1 M NaHCO3. Cross-links were reversed by heating at 65° C. for 4 h after adding NaCl to 200 mM final concentration. After treatment with proteinase K (50 µg/ml) for 1 h at 37° C., DNA was purified using Geneclean Turbo Kit (Q-Biogene, MP Biomedicals, Illkirch, France). Real time PCR analysis of inputs or immunoprecipitated DNAs was performed.

Quantitative Real Time PCR Analysis

Quantitative real time PCR was performed with standard protocols using SYBR®Green ROX Mix (ABgene, Courtaboeuf, France) as a fluorescent detection dye in ABI PRISM® 7000 in a final volume of 10 µl which also contains 300 nM of primers (Operon, Cologne, Germany)

The relative amounts of DNA in samples were determined on the basis of the threshold cycle for each PCR product (Ct).

Statistical Analysis

All values are displayed as means and standard error of the mean (SEM) within each group (Systat v 8.0, SPSS Inc., Chicago, Ill.). Statistical analysis was performed and comparison between groups were done using ANOVA and post-hoc test LSD. Survival analysis was performed using Kaplan-Meier analysis.

Results

The mode of action of therapeutic molecules for the treatment of SMA may include the increase of SMN expression particularly in motor neurons through activating the SMN2 promoter, increasing exon-7 inclusion in SMN transcripts, or extending the half-life of SMN mRNA or protein.

It may also include the promotion of motor neuron survival through the activation of anti-apoptotic pathways. Over the years, a number of groups have identified SMN2 gene-inducing compounds using cultured fibroblasts derived from SMA patients, and which benefits were often further tested in vivo in SMA mouse models[5]. Among those, SMN inducer compounds were identified based on their supposed ability to increase general gene expression, such as histone deacetylase inhibitors[6, 7, 8], or by high throughput screenings, such as quinazoline derivatives[9, 10]. Unfortunately, to date, many of these compounds were disappointing in clinical trials with no substantial clinical benefit demonstrated[11, 12, 13]. Ultimately, none of these compounds provide efficient anti-apoptotic potential for motor neurons.

One promising, as yet unexplored, therapeutic development for SMA could involve the pharmacological correction of molecular mechanisms, specifically altered in SMA neuromuscular system, potentially capable of modulating either SMN expression, or motor-neuron survival or both. In this context, the inventors paid further attention to the activation pattern of the AKT/CREB signalling pathway. Constitutively down-regulated in mouse SMA spinal cord, the AKT/CREB pathway is able to remarkably alleviate SMA symptoms in mice as long as it is reactivated[14]. In very severe SMA-like mice[15], the reactivation of AKT/CREB pathway by NMDA resulted in an increased in the total amount of SMN transcripts in the SMA spinal cord without modifying its splicing pattern suggesting a SMN2 gene regulation at the transcriptional level[14]. Furthermore, considered as a common and powerful antiapoptotic pathway[16] notably for spinal motor neurons[17], the AKT/CREB pathway activation likely represents an important clue for motor neuron resistance to cell death in SMA spinal cord. Thus, identifying therapeutic agents that could lead to the reactivation of the AKT/CREB pathway in SMA spinal cord is of a paramount importance.

Interestingly, the activation profile of another major intracellular signaling pathway in neurons[18], namely the ERK1/2 signaling pathway, was in opposite contrast to that of AKT in SMA spinal cord. Constitutively over-activated in the spinal cord of two different severe mouse models of SMA, characterized by a weak SMN expression, ERK1/2 was inhibited when AKT is reactivated and this change in ERK/AKT activation balance correlated with an increase in SMN expression[14]. These data raise important questions regarding 1) the respective roles of ERK and AKT pathways in modulating SMN2 gene expression and 2) the potential cross relationships in the activation profile of these two signaling pathways in SMA spinal cord.

Interestingly, the sequence analysis of the human SMN promoter (GenBank accession AF187725) revealed that several CREB binding sites are flanked by putative response elements for transcription factors that are direct target of ERK[19, 20, 21], namely the transcription factors of the ETS family Elk-1 (FIG. 1*a-b*). Yet, the CREB binding site 2 (+244 to +248 bp), considered as a positive regulator of SMN gene expression[22], contains also putative response elements for Elk-1 (+356 to +429 bp), including a binding site for the Serum Response Factor (SRF). We identified an additional putative CRE site, which we named site 1, that includes two putative CREB binding sites (−2572 to −2569 by and −2525 to −2522 bp) also containing putative SRF binding site (−2556 to −2548 bp). ChIP experiments showed that the two transcription factors effectively bound to the two CRE sites but with an efficacy that correlated to their levels of activation. Elk-1, over-activated in the spinal cord of type 1 SMA-like mice (FIG. 1*c-d*), as expected for a direct target of ERK, displayed an increased binding on the two CRE sites in SMA spinal cord compared to controls (FIG. 1*e-f*). In contrast, ChIP experiments revealed a dramatic decrease in the binding of CREB to the two CRE sites (FIG. 1*g-h*). Interestingly, the ratio of CREB and Elk-1 binding on the CRE sites was completely reversed in SMA spinal cords when SMN expression is promoted i.e. after a direct NMDA-receptor activation (FIG. 1*e-h*). To gain further insight into the potential role of Elk-1 in the control of SMN2 gene expression, we analysed by ChIP the acetylation profiles of histones H3 and H4 in the two CRE sites in the spinal cord of SMA and control mice. Elk-1 recruitment to the two CRE sites correlated to a marked decrease of H3 and H4 acetylation, compared to controls, whereas CREB recruitment induced a marked increase of H3 and H4 acetylation (FIG. 1*i-l*). Taken together, these results suggested that the ERK/Elk-1 pathway activation resulted in the repression of SMN2 gene expression in SMA spinal cord, contrasting with the results found in a non SMA neuronal context[23].

Therefore, it could be speculated that inhibiting the ERK pathway would abolish the Elk-1-induced inhibition of SMN2 gene transcription and would lead consequently to an increase of SMN expression in SMA spinal cord. To test this hypothesis, a population of type 1 SMA-like mice was treated daily from birth by intrathecal injection of U0126, a specific MAPK Kinase (MEK) inhibitor. The in vivo ERK inhibition, that induced a marked decrease of Elk-1 activation in SMA (FIG. 2*a-b*), resulted in a remarkable increase in SMN protein concentration in the spinal cord of type 1 SMA-like mice (FIG. 2*c-d*). These data are further emphasized by the significant increase of gemini of coiled bodies (gems) in the motor-neuron nuclei of U0126-treated SMA-like mice (data not shown and FIG. 2*e*). Unexpectedly, the ERK inhibition resulted in a significant activation of AKT (FIG. 2*f-g*) and CREB (FIG. 2*h-i*) in SMA spinal cord, likely acting synergistically with the Elk-1 inhibition to increase SMN expression. Consistent with our findings in SMA-like mice, the inhibition of the ERK pathway by U0126 in myotube culture of paravertebral muscles from type 2 SMA patient resulted in a significant increase of SMN expression (FIG. 2*j-k*).

In order to substantiate this crosstalk hypothesis at the level of the kinases ERK and AKT in the signaling cascades, we tested in vitro the effects of CREB inhibition on the ERK/Elk-1 pathway activation profile in a SMA context in which the AKT pathway was significantly activated i.e. following NMDA-receptor activation. We found that CREB inhibition resulted in the activation of ERK1/2 (FIG. 3*a-b*) and Elk-1 (FIG. 3*c-d*) as hypothesized. More surprisingly, the CREB inhibition resulted in a significant inhibition of the AKT (FIG. 3*e-f*), suggesting a negative feedback from the transcription factor to its activating kinase. The concomitant activation of the ERK/Elk-1 pathway and inhibition of the AKT/CREB pathway expectedly resulted in a significant decrease in SMN expression (FIG. 3*g-h*). Taken together, these data strongly suggest the existence of a dynamic equilibrium between ERK and AKT pathways in SMA spinal cord. This equilibrium could be displaced by reciprocal blockades, opening thus a promising way for reactivating the AKT/CREB pathway in SMA spinal cord.

Finally, in vivo ERK inhibition resulted in a remarkable improvement in the phenotype and survival of severe SMA-like mice compared to vehicle-treated counterparts. The mean survival increased from 1.60±0.48 days for the vehicle-treated SMA-like mice to 4.13±1.07 days for the U0126-treated mice (FIG. 4*a*), representing a 2.5 fold increase in lifespan ($p<0.01$), which remains, to date, the best pharmacological treatment ever reported in this SMA mouse model. In addition, the U0126 treatment led to a significant and progressive increase in the body weight of SMA-like mice, until death (FIG. 4b). These benefits were associated with the significant increase in the number and the surface of motor-neuron in lumbar spinal cord of U0126-treated SMA-like mice compared to placebos (FIG. 4c-h).

These results prompted us to test whether a pre-approved MEK inhibitor could provide the same effects of U0126 on SMN expression and severe SMA-like mouse lifespan. We chose to test a new drug, Selumetinib (AZD6244), a well known specific MEK inhibitor, which is currently in phase II clinical trial[4], successfully tested in the Pediatric Preclinical Testing[24]. Expectedly, oral Selumetinib treatment reproduced the effects obtained with U0126, including an activation of SMN expression in the spinal cord of SMA mice (FIG. 4i-j), an activation of AKT (FIG. 4k-l) and a remarkable increase in the life span of SMA mice (FIG. 4m) associated with a progressive gain of body weight (FIG. 4n).

Taken together, all these results indicate that the pharmacological inhibition of ERK pathway, notably through the use of Selumetinib, could be considered as an efficient treatment to alleviate SMA symptoms in patients.

REFERENCES

1—Crawford, T. O. & Pardo, C. A. The neurobiology of childhood spinal muscular atrophy. *Neurobiol. Dis.* 3, 97-110 (1996).
2—Lefebvre, S. et al. Identification and characterization of a spinal muscular atrophy-determining gene. *Cell* 80, 155-165 (1995).
3—Lorson, C. L. & Androphy, E. J. An exonic enhancer is required for inclusion of an essential exon in the SMA-determining gene SMN. *Hum. Mol. Genet.* 9, 259-265 (2000).
4—Board, R. E. et al. Detection of BRAF mutations in the tumour and serum of patients enrolled in the AZD6244 (ARRY-142886) advanced melanoma phase II study. *Br. J. Cancer* 101, 1724-1730 (2009).
5—Lorson, C. L., Rindt, H. & Shababi, M. Spinal muscular atrophy: mechanisms and therapeutic strategies. *Hum. Mol. Genet.* 19, R111-118 (2010).
6—Chang, J. G. et al. Treatment of spinal muscular atrophy by sodium butyrate. *Proc. Natl. Acad. Sci. U.S.A.* 98, 9808-9813 (2001).
7—Avila, A. M. et al. Trichostatin A increases SMN expression and survival in a mouse model of spinal muscular atrophy. *J. Clin. Invest.* 117, 659-671 (2007).
8—Tsai, L. K., Tsai, M. S., Ting, C. H. & Li, H. Multiple therapeutic effects of valproic acid in spinal muscular atrophy model mice. *J. Mol. Med.* 86, 1243-1254 (2008).
9—Thurmond, J. et al. Synthesis and biological evaluation of novel 2,4-diaminoquinazoline derivatives as SMN2 promoter activators for the potential treatment of spinal muscular atrophy. *J. Med. Chem.* 51, 449-469 (2008).
10—Butchbach, M. E. et al. Effect of diet on the survival and phenotype of a mouse model for spinal muscular atrophy. *Biochem. Biophys. Res. Commun.* 391, 835-840 (2010).
11—Mercuri, E. et al. Randomized, double-blind, placebo-controlled trial of phenylbutyrate in spinal muscular atrophy. *Neurology* 68, 51-55 (2007).
12—Swoboda, K. J. et al. Phase II open label study of valproic acid in spinal muscular atrophy. PLoS One 4, e5268. (2009).
13—Swoboda, K. J. et al. Project Cure Spinal Muscular Atrophy Investigators Network. SMA CARNI-VAL trial part I: double-blind, randomized, placebo-controlled trial of L-carnitine and valproic acid in spinal muscular atrophy. *PLoS One* 5, e12140 (2010).
14—Biondi, O. et al. In vivo NMDA receptor activation accelerates motor unit maturation, protects spinal motor neurons, and enhances SMN2 gene expression in severe spinal muscular atrophy mice. *J. Neurosci.* 30, 11288-11299 (2010).
15—Monani, U. R. et al. The human centromeric survival motor neuron gene (SMN2) rescues embryonic lethality in Smn(−/−) mice and results in a mouse with spinal muscular atrophy. *Hum. Mol. Genet.* 9, 333-339 (2000).
16—Dudek, H. et al. Regulation of neuronal survival by the serine-threonine protein kinase AKT. *Science* 275, 661-665 (1997).
17—Soler, R. M. et al. Receptors of the glial cell line-derived neurotrophic factor family of neurotrophic factors signal cell survival through the phosphatidylinositol 3-kinase pathway in spinal cord motoneurons. *J. Neurosci.* 19, 9160-9169 (1999).
18—Xia, Z., Dickens, M., Raingeaud, J., Davis, R. J., Greenberg, M. E. Opposing effects of ERK and JNK-p38 MAP kinases on apoptosis. *Science* 270, 1326-1331 (1995).
19—Whitmarsh, A. J., Shore, P., Sharrocks, A. D. & Davis, R J. Integration of MAP kinase signal transduction pathways at the serum response element. *Science* 269, 403-407 (1995).
20—Yang, S. H., Shore, P., Willingham, N., Lakey, J. H. & Sharrocks, A. D. The mechanism of phosphorylation-inducible activation of the ETS-domain transcription factor Elk-1. *EMBO J.* 18, 5666-5674 (1999).
21—Zhang, H. M. Mitogen-induced recruitment of ERK and MSK to SRE promoter complexes by ternary complex factor Elk-1. *Nucleic Acids Res.* 36, 2594-2607 (2008).
22—Majumder, S. et al. Identification of a novel cyclic AMP-response element (CRE-II) and the role of CREB-1 in the cAMP-induced expression of the survival motor neuron (SMN) gene. *J. Biol. Chem.* 279, 14803-14811 (2004).
23—Demir, O. et al. ETS-domain transcription factor Elk-1 mediates neuronal survival: SMN as a potential target. *Biochim. Biophys. Acta* 1812, 652-662. (2011).
24—Kolb, E. A, et al. Initial testing (stage 1) of AZD6244 (ARRY-142886) by the Pediatric Preclinical Testing Program. *Pediatr. Blood Cancer* 55, 668-677 (2010).
25—Kobayashi, T., Askanas, V. & Engel, W. K. Human muscle cultured in monolayer and cocultured with fetal rat spinal cord: importance of dorsal root ganglia for achieving successful functional innervation. *J. Neurosci.* 7, 3131-3141 (1987).
26—Bigot, A. et al. Large CTG repeats trigger p16-dependent premature senescence in myotonic dystrophy type 1 muscle precursor cells. *Am. J. Pathol.* 174, 1435-1442 (2009).
27—Towbin, H., Schoenenberger, C., Ball, R., Braun, D. G. & Rosenfelder, G. Glycosphingolipid-blotting: an immunological detection procedure after separation by thin layer chromatography. *J. Immunol. Methods.* 72, 471-479 (1984).

The invention claimed is:

1. A method of treating spinal muscular atrophy in a subject in need thereof comprising:
   administering to the subject an effective amount of an ERK inhibitor;
   wherein said ERK inhibitor is a selective MEK inhibitor; and
   wherein said spinal muscular atrophy is associated with deficiency in a Survival-Motor-Neuron gene, said deficiency resulting in loss of motor function.

2. The method according to claim 1, wherein said deficiency resulting in loss of motor function is a genetic mutation in Survival-Motor-Neuron 1 gene.

3. The method according to claim 1, wherein said ERK inhibitor is a MEK½ inhibitor.

4. The method according to claim 3, wherein said MEK½ inhibitor is selected from selumetinib, U0126, PD98059, PD0325901, AZD8330, CI-1040 and PD318088.

5. The method according to claim 3, wherein said ERK inhibitor is selected from the group consisting of selumetinib and its derivatives and pharmaceutically acceptable salts thereof.

6. The method according to claim 1, wherein said ERK inhibitor is selected from the group consisting of nucleic acid molecule, siRNA, shRNA and anti-sense oligonucleotide; said nucleic acid molecule reducing the expression of MEK1, MEK2, ERK1 or ERK2.

7. The method according to claim 1, wherein said ERK inhibitor is administered orally to a subject in an amount effective to treat spinal muscular atrophy.

8. A method of treating spinal muscular atrophy in a subject in need thereof comprising:
   administering to the subject an effective amount of at least one agent selected from selumetinib, U0126, PD98059, PD0325901, AZD8330, CI-1040 and PD318088.

9. The method of claim 3 wherein, the ERK inhibitor has an IC50 of at least 1μM, or less.

10. The method according to claim 3, wherein said ERK inhibitor is selected from the group consisting of U0126 and its derivatives and pharmaceutically acceptable salts thereof.

11. The method according to claim 8, comprising administering to the subject an effective amount of U0126.

12. The method according to claim 8, comprising administering to the subject an effective amount of selumetinib.

* * * * *